(12) United States Patent
Reiter

(10) Patent No.: US 9,470,689 B2
(45) Date of Patent: *Oct. 18, 2016

(54) N-CADHERIN: TARGET FOR CANCER DIAGNOSIS AND THERAPY

(71) Applicant: The Regents of the University of California, Oakland, CA (US)

(72) Inventor: Robert E. Reiter, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/145,556

(22) Filed: Dec. 31, 2013

(65) Prior Publication Data

US 2014/0220005 A1   Aug. 7, 2014

Related U.S. Application Data

(63) Continuation of application No. 12/268,302, filed on Nov. 10, 2008, now Pat. No. 8,663,635, which is a continuation-in-part of application No. 12/294,023, filed as application No. PCT/US2007/007083 on Mar. 21, 2007, now abandoned.

(60) Provisional application No. 60/784,734, filed on Mar. 21, 2006.

(51) Int. Cl.
| | |
|---|---|
| *A61K 39/00* | (2006.01) |
| *G01N 33/574* | (2006.01) |
| *C07K 16/28* | (2006.01) |
| *C07K 16/30* | (2006.01) |

(52) U.S. Cl.
CPC ..... *G01N 33/57492* (2013.01); *C07K 16/2896* (2013.01); *C07K 16/3038* (2013.01); *C07K 16/3069* (2013.01); *G01N 33/57407* (2013.01); *G01N 33/57434* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,750,078 A | 5/1998 | Shitara et al. | |
| 5,889,157 A | 3/1999 | Pastan et al. | |
| 6,472,368 B1 * | 10/2002 | Doherty et al. | 514/19.1 |
| 6,682,901 B2 | 1/2004 | Blaschuk et al. | |
| 7,973,139 B2 | 7/2011 | Bell et al. | |
| 2002/0146687 A1 | 10/2002 | Blaschuk et al. | |
| 2003/0190602 A1 | 10/2003 | Pressman et al. | |
| 2004/0248219 A1 | 12/2004 | Blaschuk et al. | |
| 2007/0105133 A1 | 5/2007 | Clarke et al. | |
| 2010/0119527 A1 | 5/2010 | Reiter | |
| 2010/0233170 A1 | 9/2010 | Reiter et al. | |
| 2010/0278821 A1 | 11/2010 | Reiter | |
| 2011/0086029 A1 | 4/2011 | Reiter et al. | |

FOREIGN PATENT DOCUMENTS

| | | |
|---|---|---|
| JP | 2002-513937 | 5/2002 |
| WO | 99/57565 | 11/1999 |
| WO | 01/62208 | 8/2001 |
| WO | 2004/106380 | 12/2004 |
| WO | 2005/061544 | 7/2005 |
| WO | 2007/109347 | 9/2007 |
| WO | 2009/124281 | 10/2009 |
| WO | 2010/054377 | 5/2010 |
| WO | 2010/054397 | 5/2010 |
| WO | 2012/021841 | 2/2012 |

OTHER PUBLICATIONS

Derycke et al, abstract, table 1, Int J. Blolo 48: 463-476, 2004.*
Clinical trial report of ADH-1(AdherEx, May 2005.*
Alexander et al., "N-cadherin Gene Expression in Prostate Carcinoma Is Modulated by Integrin-Dependent Nuclear Translocation of Twist1," Cancer Research, Apr. 1, 2006, vol. 66, No. 7, pp. 3365-3369.
Beckman et al., "Antibody Construct in Cancer Therapy, Protein Engineering Strategies to Improve Exposure in Solid Tumors," Can., 2007, Vol.109, pp. 170-179.
Blaschuk et al., "Identification of a Cadherin Cell Adhesion Recognition Sequence," Developmental Biology, 1990, vol. 139, No. 1, pp. 227-229.
Buesa et al., "DNA chip technology in brain banks: confronting a degrading world," J. Neuropathol. Exp. Neurol., 2004, vol. 63, No. 10, pp. 1003-1014, Abstract.
Bussemakers et al., "The role of OB-cadherin in in human prostate cancer," *Proceedings of the Annual Meeting of the American Association for Cancer Research*, New York, NY, Mar. 1, 1998, vol. 39, Abstract No. 3405, 1 page.
Casset et al., "A peptide mimetic of an anti-CD4 monoclonal antibody by rational design," Biochemical and Biophysical Research Communications, 2003, 307(1): 198-205.
Caldas et al., "Humanization of the anti-CD18 antibody 6.7: an unexpected effect of a framework residue in binding to antigen," Mol. Immunol., 2003, 39(15): 941-952.
Cespedes et al., "Mouse models in oncogenesis and cancer therapy," Clin. Transls. Oncol., 2006, vol. 8, No. 5, pp. 318-329.
Chien et al., "Significant structural and functional change of an antigen-binding site by a distant amino acid substitution: Proposal of a structural mechanism," Proc. Natl. Acad. Sci. USA, 1989, 86(14):5532-5536.
Clinical trial report of ADH-1, AdherEx, May 2005.

(Continued)

*Primary Examiner* — Lei Yao
(74) *Attorney, Agent, or Firm* — Riverside Law LLP

(57) ABSTRACT

The present invention provides methods of diagnosis, providing a prognosis and a therapeutic target for the treatment of cancers that express N-cadherin, including prostrate and bladder cancers.

11 Claims, 10 Drawing Sheets

(56) References Cited

OTHER PUBLICATIONS

Dennis, "Off by a whisker," *Nature*, 2006, vol. 442, pp. 739-741.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody ," J. Immunol., 2002,169(6): 3076-3084.
Fujimori, K. et al., "A Modeling Analysis of Monoclonal Antibody Percolation Through Tumors: A Binding-Site Barrier," *J. Nuc. Med.*, 1990, vol. 31, pp. 1191-1198.
International Search Report mailed on Jun. 28, 2010, for International Application No. PCT/US2009/063921 filed on Nov. 10, 2009, 1 page.
Giusti et al., "Somatic diversification of S107 from an antiphosphocholine to an anti-DNA autoantibody is due to a single base change in its heavy chain variable region," Proc. Natl. Acad. Sci. USA, May 1987, 84(9) 2926-2930.
Greenspan et al., "Defining epitopes: It's not as easy as it seems," Nature Biotechnology, 1999,7: 936-937.
Gussow et al., "Immunization of Monoclonal Antibodies," Methods in Enzymology, 1991, 203:99-121.
Holm et al., "Functional mapping and single chain construction of the anti-cytokeratin 8 monoclonal antibody TS1," Mol. Immunol., 2007, 44(6):1075-1084.
International Search Report mailed on Aug. 21, 2008, for PCT Application No. PCT/US07/07083 filed on Mar. 21, 2007, 2 pages.
Jaggi, M. et al., "N-Cadherin Switching Occurs in High Gleason Grade Prostate Cancer," *The Prostate*, 2006, vol. 66, pp. 193-199.
Harrison, O.J, et al., "The mechanism of cell adhesion by classical cadherins: the role of domain 1," Journal of Cell Science, 2005, vol. 118, No. 4, pp. 711-721.
Hatta et al., "Cloning and Expression of cDNA Encoding a Neural Calcium-dependent Cell Adhesion Molecule: Its Identity in the Cadherin Gene Family," The Journal of Cell Biology, 1988, vol. 106, No. 3, pp. 873-881.
Kim, J. et al., "N-Cadherin Extracellular Repeat 4 Mediates Epithelial to Mesenchymal Transition and Increased Motility," J of Cell Biology, 151 (6):1193-1205 (Dec. 11, 2000).
MacCallum et al., "Antibody-antigen Interactions: Contact Analysis and Binding Site Topography," J. Mol. Biol., 1996, 262 (5):732-745.
Mariuzza et al., "The Structural Basis of Antigen-Antibody Recognition," Annu. Rev. Biophys. Chem., 1987, 16:139-159.
Meyer, S. et al., "Messenger RNA Turnover in Eukaryotes: Pathways and Enzymes," *Clin. Rev. Biochem. & Molec. Biol.*, 2004, vol. 39, pp. 197-216.
Mialhe, A. et al., "Expression of E- P-, n-cadherins and Catenins in Human Bladder Carcinoma Cell Lines," *J. Urol.*, Sep. 2000, vol. 164 (3 Pt 1), pp. 826-835, Abstract Only.
Price, J.T. et al., "Mechanisms of Tumor Invasion and Metastasis: Emerging Targets for Therapy," Expert Opin. Ther. Targets, 2002, vol. 6, No. 2, pp. 217-233.
Rudikoff et al., "Single amino acid substitution altering antigen-binding specificity," Proc. Natl. Acad. Sci. USA, 1982, 79:1979-1983.
Rudnick, Can. Biotherp and Radiopharm vol. 24, p. 155-162,2009.
Rieger-Christ et al., "Novel expression of N-cadherin elicits in vitro bladder cell invasion via the Akt signaling pathway," Oncogene, 2004, vol. 23, pp. 4745-4753.
Sheets et al., "Efficient construction of a large non immune phage antibody library: The production of high-affinity human single-chain antibodies to protein antigens," Proceeding of the National Academy of Sciences, National Academy of Sciences, US, 1998, vol. 95, No. 11, pp. 6157-6162.
Supplementary Partial European Search Report mailed on Apr. 22, 2009, for EP Application No. 07753691.0, 5 pages.
Takeichi et al., "Cadherins: A Molecular Family Important in Selective Cell-Cell Adhesion," Annual Review of Biochemistry, 1990, vol. 59, No. 1, pp. 237-252.
Talmadge, J.E. et al., "Murine Models to Evaluate Novel and Conventional Therapeutic Strategies for Cancer," *Am. J. Pathol.*, 2007, vol. 170, No. 3, pp. 793-804.
Tanaka et al., "Monoclonal antibody targeting of N-cadherin inhibits prostate cancer growth, 10 metastasis and castration resistance," Nature Medicine, 2010, vol. 16, No. 12, pp. 1414-1420.
Thurber, G.M. et al., "Antibody tumor penetration: Transport opposed by systemic and antigen-mediated clearance," *Adv. Drug Deliv. Rev.*, 2008, vol. 60, pp. 1421-1434.
Tomita, K. et al., "Cadherin Switching in Human Prostate Cancer Progression," Cancer Research, Jul. 1, 2000, vol. 60, pp. 3650-3654.
Tran, N.L. et al., "N-Cadherin Expression in Human Prostate Carcinoma Cell Lines," American Journal of Pathology, Sep. 1999, vol. 155, No. 3, pp. 787-798.
Vajdos et al., "Comprehensive Functional Maps of the Antigen-binding Site of an Anti-ErbB2 Antibody Obtained with Shotgun Scanning Mutagenesis," J. Mol. Biol., 2002, 320(2): 415-428.
Voskoglou-Nomikos, T., "Clinical Predictive Value of the in vitro Cell Line, Human 14 Xenograft, and Mouse Allograft Preclinical Cancer Models," *Clin. Can. Res.*, 2003, vol. 9, pp. 4227-4239.
Wallerand, H. et al., •P-AKT Pathway Activation and Inhibition Depends on N-Cadherin or P-EGFR Expression in Invasive Human Bladder Cancer Cell Lines, Journal of Urology & Annual Meeting of the American-Urological-Association, San Antonio, TX, May 21-26, 2005, Abstract No. 582, 1 page.
Wallerland et al., "Phospho-Akt pathway activation and inhibition depends on N-cadherin 12 or phospho-EGFR expression in invasive human bladder cancer cell lines," Urologic Oncology, 2010, vol. 28, No. 2, pp. 180-188.
Williams et al., "Identification of an N-cadherin Motif That Can Interact with the Fibroblast 13 Growth Factor Receptor and Is Required for Axonal Growth," The Journal of Biological Chemistry, 2001, vol. 276, No. 47, pp. 43879-43886.
Winkler et al., "Changing the Antigen Binding Specificity by Single Point Mutations of an Anti-p24 (HIV-1) Antibody," J. Immunol., 2000,165(8):4505-4514.

* cited by examiner

FIG. 5A

Human N-Cadherin Protein Sequence Information

```
  1 mcriagairt lpilaallqa sveasgeial cktqfpedvy savlskdvhe gqpllnvkfs
 61 ncngkrkvqy essepadfkv dedgmvyavr sfplssehak fliyaqdket qekwqvavkl
121 sikptltees vkesaeveei vfprqfskhs ghlqrqkrdw vippinlpen srgpfpqelv
181 rirsdrdknl slrysvtgpg adqpptgifi inpisgqlsv tkpldreqia rfhlrahavd
241 ingnqvenpi divinvidmn dnrpeflhqv wngtvpegsk pgtyvmtvta idaddpnaln
301 gmlryrivsq apstpspnmf tinnetgdii tvaagldrek vqqytliiqa tdmegnptyg
361 lsntatavit vtdvndnppe ftamtfygev penrvdiiva nltvtdkdqp htpawnavyr
421 isgqdptgrf aiqtdpnsnd glvtvvkpid fetnrmfvlt vaaenqvpla kgighppqst
481 atvsvtvidv nenpyfapnp kiirqeeglh agtmlttfta qdpdrymqqn irytklsdpa
541 nwikidpvng qittiavldr espnvknniy natflasdng ippmsgtgtl qiyildindn
601 apqvlpqeae tcetpdpnsi nitaldydid pnagpfafdl plspvtikrn wtitrlngdf
661 aqlnlkikfl eagiyevpii itdsgnppks nisilrvkvc qcdsngdctd vdrivgaglg
721 tgaiiaillc iiillilvlm fvvwmkrrdk erqakqllid peddvrdnil kydeegggee
781 dqdydlsqlq qpdtvepdai kpvgirrmde rpihaepqyp vrsaaphpgd igdfineglk
841 aadndptapp ydsllvfdye gsgstlgsls slnsssggde qdydylndwg prfkkladmy
901 gggdd
``` mRNA

ORIGIN

```
   1 atgtgccgga tagcgggagc gctgcggacc ctgccgctgc tggcggccct gcttcaggcg
  61 tctgtagagc cttctggtga aatcgcatta tgcaagactg gatttcctga agatgtttac
 121 agtgcagtct tatcgaagga tgtgcatgaa ggacgcctc ttctcaatgt gaagtttagc
 181 aactgcaatg gaaaagaaa agtacaatat gagagcagtg agcctgcaga ttttaaggtg
 241 gatgaagatg gcatggtgta tgccgtgaga agctttccac tctcttctga gcatgccaag
 301 ttcctgatat atgcccaaga caaagagacc caggaaaagt ggcaagtggc agtaaaattg
 361 agcctgaagc caaccttaac tgaggagtca gtgaaggagt cagcagaagt tgaagaaata
 421 gtgttcccaa gacaattcag taagcacagt ggccacctac aaaggcagaa gagagactgg
 481 gtcatcctc caatcaactt gccagaaaac tcagggac cttttcctca agagcttgtc
 541 aggatcaggt ctgatagaga taaaaacctt tcactgcggt acagtgtaac tgggccagga
 601 gctgaccagc ctccaactgg tatcttcatt atcaacccca tctcgggtca gctgtcggtg
 661 acaaagcccc tggatcgcga gcagatagcc cggttcatt tgagggcaca tgcagtagat
 721 attaatggaa atcaagtgga gaacccatt gacattgtca tcaatgttat tgacatgaat
 781 gacaacagac ctgagttctt acaccaggtt tggaatggga cagttcctga gggatcaaag
 841 cctggaacat atgtgatgac cgtaacagca attgatgctg acgattcacc tgccatgttt
 901 gggatgttga ggtacagaat cgtgtctcag gctccaagca cccttcacc caacatgttt
 961 acaatcaaca atgagactgg tgacatcatc acagtggcag ctggacttga tcgagaaaaa
1021 gtgcaacagt atacgttaat aattcaagct acagacatgg aaggcaatcc cacatatggc
1081 ctttcaaaca cagccacggc cgtcatcaca gtgacagatg tcaatgacaa tcctccagag
1141 tttactgcca tgacgtttta tggtgaagtt cctgagaaca gggtagacat catagtagct
1201 aatctaactg tgaccgataa ggatcaaccc catacaccag cctggaacgc agtgtacaga
1261 atcagtggcg gagatcctac tggacggttc gccatccaga ccgacccaaa cagcaacgac
1321 gggttagtca ccgtggtcaa accaatcgac tttgaaacaa ataggatgtt tgtccttact
1381 gttgctgcag aaaatcaagt gccattagcc aagggaattc agcaccggcc tcagtcaact
1441 gcaaccgtgt ctgttacagt tattgacgta aatgaaaacc cttatttgc cccaatcct
1501 aagatcattc gccagaaga agggcttcat gccggtacca tgttgacaac attcactgct
1561 caggaccag atcgatatat gcagcaaaat attagataca ctaaattatc tgatcctgcc
1621 aattggctaa aaatagatcc tgtgaatgga caaataacta caattgctgt tttggaccga
1681 gaatccacaa atgtgaaaaa caatatatat aatgctactt tcctgcttc tgacaatgga
1741 attcctccta tgagtggaac aggaacgctg cagatctatt tacttgatat taatgacaat
1801 gccctcaag tgttacctca agaggcagag acttgcgaaa ctccagaccc caattcaatt
1861 aatattacag cacttgatta tgacattgat ccaaatgctg gaccatttgc ttttgatctt
1921 ccttatctc cagtgactat taagagaaat tggaccatca ctcggcttaa tggtgatttt
1981 gctcagctta attaaagat aaaatttctt gaagctggta tctatgaagt tcccatcata
2041 atcacagatt cgggtaatcc tcccaaatca aatatttca tcctgcgcgt gaaggtttgc
```

FIG. 5B

```
2101 cagtgtgact ccaacgggga ctgcacagat gtggacagga ttgtgggtgc ggggcttggc
2161 acggtgcca tcattgccat cctgctctgc atcatcatcc tgcttatcct tgtgctgatg
2221 tttgtggtat ggatgaaacg ggggataaa gaacgccagg ccaaacaact tttaattgat
2281 ccagaagatg atgtaagaga taatatttta aaatatgatg aagaaggtgg aggagaagaa
2341 gaccaggact atgacttgag ccagctgcag cagcctgaca ctgtggagcc tgatgccatc
2401 aagcctgtgg gaatccgacg aatggatgaa agacccatcc acgctgagcc ccagtatccg
2461 gtccgatctg cagccccaca ccctggagac attggggact tcattaatga gggccttaaa
2521 gcggctgaca atgacccac agctccacca tatgactccc tgttagtgtt tgactatgaa
2581 ggcagtggct ccaccttggg gtccttgagc tcccttaatt cctcaagtag tggtggtgag
2641 caggactatg attacctgaa cgactggggg ccacggttca agaaacttgc tgacatgtat
2701 ggtggaggtg atgactga
``` translation = "MCRIAGALRTLPLLAALLQASVEASGEIALCKTGFPEDVYSAVL
SKDVHEGQPLLRVKFSNCNGKRKVQYESSEPADFKVDEDGMVYAVRSFPLSSEHAKFL
IYAQDKETQEKWQVAVRLSLKPTLTEESVKESAEVEEIVFPRQFSKHSGHLQRQKRDW
VIPPINLPENSRGPFPQELVRIRSDRDKNLSLRYSVTGPGADQPPTGIFIINPISGQL
SVTKPLDREQIARFHLRAHAVDINGNQVENPIDIVINVIDMNDNRPEFLHQVWNGTVP
EGSKPGTYVMTVTAIDADDPNALNGMLRYRIVSQAPSTPSPNMFTINNETGDIITVAA
GLDREKVQQYTLIIQATDMEGNPTYGLSNTATAVITVTDVNDNPPEFTAMTFYGEVPE
NRVDIIVANLTVTDKDQPHTPAWNAVYRISGGDPTGRFAIQTDPNSNDGLVTVVKFID
FETNRMFVLTVAAENQVPLAKGIQHPPQSTATVSVTVIDVNERPYFAPNPKIIRQEEG
LHACTMLTTFTAQDPDRYMQQNIRYTKLSDPANWLKIDPVNGQITTIAVLDRESPNVK
NNIYNATFLASDNGIPPMSGTGTLQIYLLDINDNAPQVLPQEAETCETPDPNSIMITA
LDYDIDPNAGPFAFDLPLSPVTIKRNWTITRLNGDFAQLNLKIKFLEAGIYEVPIIIT
DSGNPPKSNISILRVKVCQCDSNGDCTDVDRIVGAGLGTGAIIAILLCIIILLILVLM
FVVWMKRRDKERQAKQLLIDPEDDVRDNILKYDEEGGEEDQDYDLSQLQQPDTVEPD
AIKPVGIRRMDERPIHAEPQYPVRSAAFHPGDIGDFINEGLKAADNDPTAPPYDSLLV
FDYEGSGSTLGSLSSLNSSSGGEQDYDYLNDWGPRFKKLADMYGGGDD"

FIG. 6A

N-Cadherin variant sequence and antibody binding information

LOCUS     NM_001792          4122 bp   mRNA    linear
DEFINITION  Homo sapiens cadherin 2, type 1, N-cadherin (neuronal) (CDH2),
      mRNA.

CDS   206..2926

MCRIAGALRTLLPLLAALLQASVEASGEIALCKTGFPEDVYSAVLSKDVHEGQPLLNVK
FSNCNGKRKVQYESSEPADFKVDEDGMVYAVRSFPLSSEHAKFLIYAQDKETQEKWQV
AVKLSLKPTLTEESVKESAEVEEIVFPRQFSKHSGHLQRQKRDWVIPPINLPENSRGPFPQ
ELVRIRSDRDKNLSLRYSVTGPGADQPPTGIFIINPISGQLSVTKPLDREQIARFHLRAHAV
DINGNQVENPIDIVINVIDMNDNRPEFLHQVWNGTVPEGSKPGTYVMTVTAIDADDPNA
LNGMLRYRIVSQAPSTPSPNMFTINNETGDIITVAAGLDREKVQQYTLIIQATDMEGNPT
YGLSNTATAVITVTDVNDNPPEFTAMTFYGEVPENRVDIIVANLTVTDKDQPHTPAWNA
VYRISGGDPTGRFAIQTDPNSNDGLVTVVKPIDFETNRMFVLTVAAENQVPLAKGIQHPP
QSTATVSVTVIDVNENPYFAPNPKIIRQEEGLHAGTMLTTFTAQDPDRYMQQNIRYTKLS
DPANWLKIDPVNGQITTIAVLDRESPNVKNNIYNATFLASDNGIPPMSGTGTLQIYLLDIN
DNAPQVLPQEAETCETPDPNSINITALDYDIDPNAGPFAFDLPLSPVTIKRNWTITRLNGD
FAQLNLKIKFLEAGIYEVPIIITDSGNPPKSNISILRVKVCQCDSNGDCTDVDRIVGAGLGT
GAIIAILLCIIILLILVLMFVVWMKRRDKERQAKQLLIDPEDDVRDNILKYDEEGGGEEDQ
DYDLSQLQQPDTVEPDAIKPVGIRRMDERPIHAEPQYPVRSAAPHPGDIGDFINEGLKAA
DNDPTAPPYDSLLVFDYEGSGSTAGSLSSLNSSSSGGEQDYDYLNDWGPRFKKLADMY
GGGDD

Binding sites of antibodies: Ncad 1H7, 2B3, 1F12 – 21-425aa ;

1 tttgtcatca gctcgctctc cattggcggg gagcggagag cagcgaagaa gggggtgggg 61 agggggagggg aagggaaggg ggtggaaact gcctggagcc gtttctccgc gccgctgttg 121 gtgctgccgc tgcctcctcc tcctccgccg ccgccgccgc cgccgccgcc tcctccggct 181 cttcgctcgg ccccctctccg cctccatgtg ccggatagcg ggagcgctgc ggaccctgct 241 gccgctgctg gcggccctgc ttcaggcgtc tgtagaggct tctgggaaa tgcattatg     Ncad 1H7, 2B3, 1F12
– 266-1482

301 caagactgga ttcctgaag atgtttacag tgcagtctta tcgaaggatg tgcatgaagg 361 acagcctctt ctcaatgtga agtttagcaa ctgcaatgga aaaagaaaag tacaatatga 421 gagcagtgag cctgcagatt ttaaggtgga tgaagatggc atggtgtatg ccgtgagaag

FIG. 6B 481 ctttccactc tcttctgagc atgccaagtt cctgatatat gcccaagaca aagagaccca 541 ggaaaagtgg caagtggcag taaaattgag cctgaagcca accttaactg aggagtcagt 601 gaaggagtca gcagaagttg aagaaatagt gttcccaaga caattcagta agcacagtgg 661 ccacctacaa aggcagaaga gagactgggt catccctcca atcaacttgc cagaaaactc 721 caggggacct ttcctcaag agcttgtcag gatcaggtct gatagagata aaaacctttc 781 actgcggtac agtgtaactg ggccagggc tgaccagcct ccaactggta tcttcattat    Mutation "g" instead of "a"

841 caaccccatc tcgggtcagc tgtcggtgac aaagccctg gatcgcgagc agatagcccg 901 gtttcatttg agggcacatg cagtagatat taatggaaat caagtggaga acccatga 961 cattgtcatc aatgttattg acatgaatga caacagacct gagttcttac accaggttg 1021 gaatgggaca gttcctgagg gatcaagcc tggaacatat gtgatgaccg taacagcaat 1081 tgatgctgac gatcccaatg ccctcaatgg gatgttgagg tacagaatcg tgtctcaggc 1141 tccaagcacc ccttcaccca acatgtttac aatcaacaat gagactggtg acatcatcac 1201 agtggcagct ggacttgatc gagaaaaagt gcaacagtat acgtaataa ttcaagctac 1261 agacatggaa ggcaatccca catatggcct ttcaaacaca gccacggccg tcatcacagt 1321 gacagatgtc aatgacaatc ctccagagtt tactgccatg acgtttatg gtgaagttcc 1381 tgagaacagg gtagacatca tagtagctaa tctaactgtg accgataagg atcaaccca 1441 tacaccagcc tggaacgcag tgtacagaat cagtggcgga gatcctactg gacggttcgc 1501 catccagacc gacccaaaca gcaacgacgg gttagtcacc gtggtcaaac caatcgactt 1561 tgaaacaaat aggatgtttg tccttactgt tgctgcagaa aatcaagtgc cattagccaa 1621 gggaattcag cacccgcctc agtcaactgc aaccgtgtct gttacagtta ttgacgtaaa 1681 tgaaaaccct tattttgccc ccaatcctaa gatcattcgc caagaagaag ggcttcatgc 1741 cggtaccatg ttgacaacat tcactgctca ggacccagat cgatatatgc agcaaaatat

FIG. 6C 1801 tagatacact aaattatctg atcctgccaa ttggctaaaa atagatcctg tgaatggaca 1861 aataactaca attgctgttt tggaccgaga atcaccaaat gtgaaaaaca atatatataa 1921 tgctactttc cttgcttctg acaatggaat tcctcctatg agtggaacag gaacgctgca 1981 gatctattta cttgatatta atgacaatgc ccctcaagtg ttacctcaag aggcagagac 2041 ttgcgaaact ccagacccca attcaattaa tattacagca cttgattatg acattgatcc 2101 aaatgctgga ccatttgctt ttgatcttcc tttatctcca gtgactatta agagaaattg 2161 gaccatcact cggcttaatg gtgattttgc tcagcttaat ttaaagataa aatttcttga 2221 agctggtatc tatgaagttc ccatcataat cacagattcg ggtaatcctc ccaaatcaaa 2281 tatttccatc ctgcgcgtga aggtttgcca gtgtgactcc aacggggact gcacagatgt 2341 ggacaggatt gtgggtgcgg ggcttggcac cggtgccatc attgccatcc tgctctgcat 2401 catcatcctg cttatccttg tgctgatgtt tgtggtatgg atgaaacgcc gggataaaga 2461 acgccaggcc aaacaacttt taattgatcc agaagatgat gtaagagata atatttaaa 2521 atatgatgaa gaaggtggag gagaagaaga ccaggactat gacttgagcc agctgcagca 2581 gcctgacact gtggagcctg atgccatcaa gcctgtggga atccgacgaa tggatgaaag 2641 acccatccac gctgagcccc agtatccggt ccgatctgca gccccacacc ctggagacat 2701 tgggggactc attaatgagg gccttaaagc ggctgacaat gaccccacag ctccaccata 2761 tgactccctg ttagtgtttg actatgaagg cagtggctcc actgctgggt ccttgagctc 2821 ccttaattcc tcaagtagtg gtggtgagca ggactatgat tacctgaacg actgggggcc 2881 acggttcaag aaactgctg acatgtatgg tggaggtgat gactgaactt cagggtgaac 2941 ttggttttg acaagtaca aacaatttca actgatattc ccaaaaagca ttcagaagct 3001 aggctttaac tttgtagtct actagcacag tgcttgctgg aggctttggc ataggctgca 3061 aaccaatttg ggctcagagg gaatatcagt gatccatact gtttggaaaa acactgagct

FIG. 6D 3121 cagttacact tgaattttac agtacagaag cactgggatt ttatgtgcct ttttgtacct 3181 ttttcagatt ggaattagtt ttctgtttaa ggcttaatg gtactgattt ctgaaacgat 3241 aagtaaaaga caaaatattt tgtggtggga gcagtaagtt aaaccatgat atgcttcaac 3301 acgcttttgt tacattgcat ttgcttttat taaaatacaa aattaaacaa acaaaaaaac 3361 tcatggagcg attttattat cttgggggat gagaccatga gattggaaaa tgtacattac 3421 ttctagtttt agactttagt ttgtttttt ttttcacta aaatcttaaa acttactcag 3481 ctggttgcaa ataaagggag ttttcatatc accaatttgt agcaaaattg aattttttca 3541 taaactagaa tgttagacac attttggtct taatccatgt acactttttt atttctgtat 3601 ttttccactt cactgtaaaa atagtatgtg tacataatgt tttattggca tagtctatgg 3661 agaagtgcag aaacttcaga acatgtgtat gtattatttg gactatggat tcaggttttt 3721 tgcatgttta tatctttcgt tatggataaa gtatttacaa aacagtgaca tttgattcaa 3781 ttgttgagct gtagttagaa tactcaatttt ttaatttttt taatttttt attttttatt 3841 ttcttttgg tttggggagg gagaaaagtt cttagcacaa atgttttaca taatttgtac 3901 caaaaaaaaa aaaaaggaaa ggaaagaaag gggtggcctg acactggtgg cactactaag 3961 tgtgtgtttt taaaaaaaaa aaatggaaaa aaaaaagctt ttaaactgga gagacttctg 4021 acaacagctt tgcctctgta tgtgtacca gaatataaat gatacacctc tgaccccagc 4081 gttctgaata aaatgctaat tttggaaaaa aaaaaaaaaa aa Note the mutation at 808. When sequenced, it's a "g" instead of an "a" as published,
codes for the same aa. The amino acids are highlighted in the attachment.

N-CADHERIN: TARGET FOR CANCER DIAGNOSIS AND THERAPY

CROSS-REFERENCE TO RELATED APPLICATIONS

The present application is a continuation of Ser. No. 12/268,302, filed Nov. 10, 2008, which is a continuation-in-part of Ser. No. 12/294,023, filed Sep. 22, 2008, which is a national phase application filed under 35 U.S.C. §371 claiming benefit to International Patent Application No. PCT/US07/07083, filed Mar. 21, 2007, which is entitled to priority under 35 U.S.C. §119(e) to U.S. Provisional Patent Application No. 60/784,734, filed Mar. 21, 2006, each of which is herein incorporated by reference in its entirety.

BACKGROUND OF THE INVENTION

Introduction

Prostate cancer is the most common malignancy and the second leading cause of cancer-related death in American men. Prostate cancer is a biologically and clinically heterogeneous disease. A majority of men with this malignancy harbor slow-growing tumors that may not impact an individual's natural lifespan, while others are struck by rapidly progressive, metastatic tumors. PSA screening is limited by a lack of specificity and an inability to predict which patients are at risk to develop hormone refractory metastatic disease. Recent studies advocating a lower PSA threshold for diagnosis may increase the number of prostate cancer diagnoses and further complicate the identification of patients with indolent vs. aggressive cancers (Punglia et al., N Engl J Med, 349: 335-342 (2003)). New serum and tissue markers that correlate with clinical outcome or identify patients with potentially aggressive disease are urgently needed (Welsh et al., Proc Natl Acad Sci USA, 100: 3410-3415 (2003)).

Recent expression profiling studies suggest that expression signatures for metastatic vs. non-metastatic tumors may reside in the primary tumor (Ramaswamy et al., Nat Genet, 33: 49-54 (2003); Sotiriou et al., Proc Natl Acad Sci USA, 100: 10393-10398 (2003)). Additional features that predispose tumors to metastasize to specific organs may also be present at some frequency in the primary tumor (Kang et al., Cancer Cell, 3: 537-549 (2003)). These recent observations suggest that novel markers of pre-metastatic or pre-hormone refractory prostate cancer may be identified in early stage disease. These markers may also play a role in the biology of metastatic or hormone refractory prostate cancer progression. Recent examples of genes present in primary tumors that correlate with outcome and play a role in the biology of prostate cancer progression include EZH2 and LIM kinase (Varambally et al., *Nature,* 419: 624-629 (2002); Yoshioka et al., *Proc Natl Acad Sci USA,* 100: 7247-7252 (2003)). However, neither of these two genes is secreted.

Here we describe a method of treating or diagnosing a cancer patient, wherein the N-cadherin protein in the cancer cells is expressed at normal or low levels, or is expressed by a subset of cancer cells and is not overexpressed. We also report a method of identifying cancer stem cells by determining the presence or absence or amount of the N-cadherin protein in test issue sample.

BRIEF SUMMARY OF THE INVENTION

In a first aspect, the present invention provides a method of treating a cancer patient, comprising the steps of: obtaining a test tissue sample from an individual at risk of having a cancer that expresses a N-cadherin protein; determining the presence or absence or amount of the N-cadherin protein in the test tissue sample in comparison to a control tissue sample from an individual known to be negative for the cancer; thereby diagnosing said cancer that expresses a N-cadherin protein, wherein the N-cadherin protein is expressed at normal or low levels, or is expressed by a subset of cells, and wherein the N-cadherin protein is not overexpressed; and administering an effective amount of N-cadherin antibody or fragment thereof to the individual at risk of having a cancer that expresses a N-Cadherin protein.

In another aspect, the present invention provides method of identifying cancer stem cells, comprising the steps of obtaining a test tissue sample from an individual at risk of having a cancer that expresses a N-cadherin protein; determining the presence or absence of cancer stem cells in the test tissue sample in comparison to a control tissue sample from an individual known to be negative for the cancer; wherein the N-cadherin protein is expressed at normal or low levels, or is expressed by a subset of the stem cells and is not overexpressed.

In one embodiment, said tissue sample is prostate or bladder tissue. In another embodiment, said cancer is a prostate cancer. In another embodiment, said cancer is a bladder cancer. In another embodiment, said cancer is a hormone refractory prostate cancer. In another embodiment, said cancer is a metastatic cancer. In another embodiment, said antibody is a monoclonal antibody. In another embodiment, the fragment is a scFv. In another embodiment, the fragment is a diabody.

In any of the above aspects and embodiments, the tissue, cancer, subject, or patient to be treated is human or mammalian. In any of the above aspects and embodiments, the cancer can be an androgen independent cancer.

BRIEF DESCRIPTION OF THE DRAWINGS

FIG. 5A to FIG. 5B and FIG. 6A through FIG. 6D: N-cadherin sequences for human N-cadherin protein (SEQ ID NO:1) and cDNA (SEQ ID NO:2) and for human N-cadherin variant CDH2 protein (SEQ ID NO:3) and cDNA (SEQ ID NO:4).

DETAILED DESCRIPTION OF THE INVENTION

Figure 1:
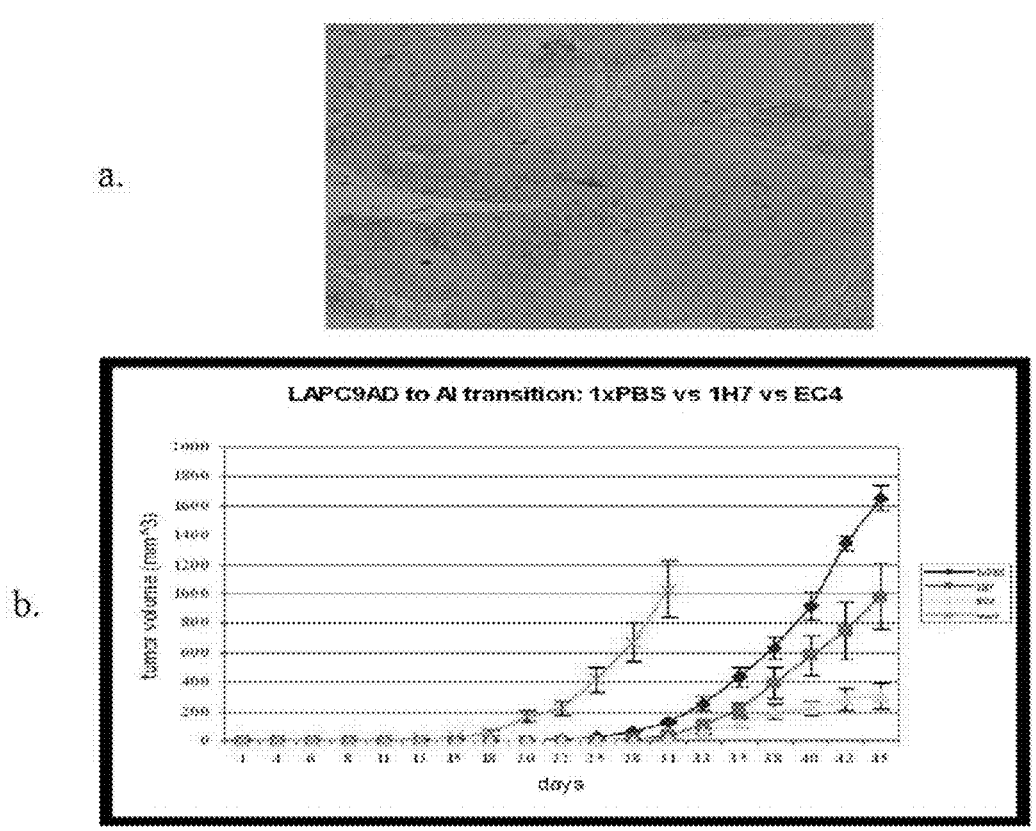
FIG. 1. (a) immunohistochemical staining of an androgen independent LAPC 9 prostate cancer, showing that N-cadherin is only expressed by a small subset of cells (b) treatment of androgen dependent and independent LAPC-9 tumors with control PBS or N-cadherin antibodies IH7 and EC4.

We report here on the identification, characterization and validation of a gene product which are expressed in hormone refractory prostate cancer and bladder cancer. These gene product is N-Cadherin.

N-cadherin does not need to be overexpressed compared to normal tissues to be a target for treatment and diagnosis. It can be expressed at low levels and also can be expressed only by a subset of cells. Data shows that targeting N-cadherin even in 5% of prostate cancer cells is sufficient to block the progression of prostate cancers to castration resistance.

N-cadherin is a target in cancer stem cells. The data showing that targeting of N-cadherin in 5% or fewer cells is sufficient to block tumor progression is consistent with the hypothesis that N-cadherin is a marker of cancer stem cells, and that inhibition of N-cadherin on these stem cells is sufficient to block growth of the tumor as a whole.

N-cadherin expressing cells, consistent with its being a cancer stem cell marker, are more tumorigenic than N-cadherin non-expressing cells. N-cadherin positive cells can give rise to N-cadherin negative cells, also consistent with the theory that N-cadherin is a novel marker of cancer stem cells. Finally, tumors must upregulate or acquire N-cadherin in order to grow. That is, tumor stem cells must acquire properties of epithelial to mesenchymal transition in order to be tumorigenic.

Accordingly, N-Cadherin is an especially promising therapeutic target for cancer therapy, including but not limited to prostate and bladder cancer. It is found on cell surfaces, overexpressed in many epithelial tumors, and is associated with invasion, metastasis and possibly androgen independence. As shown in the present invention cancer stem cells show normal or low expression of N-cadherin. Antibodies against N-cadherin therefore are a particularly preferred agent for use in treating cancers, including but not limited toepithelial, urogenital cancers (bladder, prostate), and, more particularly, their invasive or metastasized forms. In some embodiments, monoclonal antibodies directed against an extracellular domain of N-cadherin are preferred. In further embodiments, the first extracellular domain (EC1), portions of the first and second domains, or fourth extracellular domain of N-cadherin are preferred in treating these cancers. In some embodiments, use of a antibody directed toward the extracellular domain 4 is particularly preferred in these treatments as this domain is found to be important in pro-motility and invasive potential (see, Kim et al, *J. Cell Biol.* 151(6):1193-206 (2000), incorporated by reference in its entirety with respect to the definition of the various N-cadherin domains.

N-cadherin expression can contribute to prostate and bladder cancer invasion and metastasis as well as the progression of prostate cancer to hormone refractory disease. N-Cadherin can be targeted therapeutically both alone and in combination with other small molecule inhibitors of mTOR and EGFR. Targeting N-Cadherin can help prevent or control invasive and metastatic prostate cancer.

DEFINITIONS

"N-Cadherin," refers to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a respectively referenced nucleic acid or an amino acid sequence described herein, for example, as depicted in FIGS. 5 and 6, respectively; (2) specifically bind to antibodies, e.g., polyclonal antibodies, raised against an immunogen comprising a referenced amino acid sequence as depicted in FIGS. 5 and 6, respectively; immunogenic fragments respectively thereof, and conservatively modified variants respectively thereof; (3) specifically hybridize under stringent hybridization conditions to a nucleic acid encoding a referenced amino acid sequence as depicted in FIGS. 5 and 6, respectively, and conservatively modified variants respectively thereof; (4) have a nucleic acid sequence that has greater than about 95%, preferably greater than about 96%, 97%, 98%, 99%, or higher nucleotide sequence identity, preferably over a region of at least about 25, 50, 100, 150, 200, 250, 500, 1000, or more nucleotides, to a reference nucleic acid sequence as shown, respectively, in FIGS. 5 and 6. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

"Cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma. "Urogenital cancer" refers to human cancers of urinary tract and genital tissues, including but not limited to kidney, bladder, urinary tract, urethra, prostrate, penis, testicle, vulva, vagina, cervical and ovary tissues.

The cancer to be treated herein may be one characterized by low or normal expression (but not overexpression) of N-cadherin. In one embodiment of the invention, a diagnostic or prognostic assay will be performed to determine whether the patient's cancer is characterized by low or normal expression of N-cadherin. Various assays for determining such expression are contemplated and include the immunohistochemistry, FISH and shed antigen assays, southern blotting, or PCR techniques. Moreover, the N-cadherin expression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label. In some embodiments, the cancer or cancer stem cell to be treated is not yet invasive, but expresses N-cadherin.

"Therapy resistant" cancers, tumor cells, and tumors refers to cancers that have become resistant or refractory to either or both apoptosis-mediated (e.g., through death receptor cell signaling, for example, Fas ligand receptor, TRAIL receptors, TNF-R1, chemotherapeutic drugs, radiation) and non-apoptosis mediated (e.g., toxic drugs, chemicals) cancer therapies, including chemotherapy, hormonal therapy, radiotherapy, and immunotherapy.

"Low or normal expression" refers to RNA or protein expression of N-Cadherin, in a test tissue sample that is about the same or lower than RNA or protein expression of N-Cadherin in a control tissue sample. In one embodiment, the tissue sample is autologous.

The terms "cancer that expresses N-Cadherin" and "cancer associated with the expression of N-Cadherin" interchangeably refer to cancer cells or tissues that express N-Cadherin in accordance with the above definition.

The terms "cancer-associated antigen" or "tumor-specific marker" or "tumor marker" interchangeably refers to a molecule (typically protein, carbohydrate or lipid) that is preferentially expressed in a cancer cell in comparison to a normal cell, and which is useful for the preferential targeting of a pharmacological agent to the cancer cell. A marker or antigen can be expressed on the cell surface or intracellularly. Oftentimes, a cancer-associated antigen is a molecule that is overexpressed or stabilized with minimal degradation in a cancer cell in comparison to a normal cell, for instance, 2-fold overexpression, 3-fold overexpression or more in comparison to a normal cell. Oftentimes, a cancer-associated antigen is a molecule that is inappropriately synthesized in the cancer cell, for instance, a molecule that contains deletions, additions or mutations in comparison to the molecule expressed on a normal cell. Oftentimes, a cancer-associated antigen will be expressed exclusively in a cancer cell and not synthesized or expressed in a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal. Exemplified intracellular tumor markers include, for example, mutated tumor suppressor or cell cycle proteins, including p53.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, siRNA, antibody, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

Cytotoxic agents include "cell-cycle-specific" or "antimitotic" or "cytoskeletal-interacting" drugs. These terms interchangeably refer to any pharmacological agent that blocks cells in mitosis. Such agents are useful in chemotherapy. Generally, cell-cycle-specific-drugs bind to the cytoskeletal protein tubulin and block the ability of tubulin to polymerize into microtubules, resulting in the arrest of cell division at metaphase. Exemplified cell-cycle-specific drugs include vinca alkaloids, taxanes, colchicine, and podophyllotoxin. Exemplified vinca alkaloids include vinblastine, vincristine, vindesine and vinorelbine. Exemplified taxanes include paclitaxel and docetaxel. Another example of a cytoskeletal-interacting drug includes 2-methoxyestradiol.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

The design and making of siRNA molecules and vectors are well known to those of ordinary skill in the art. For instance, an efficient process for designing a suitable siRNA is to start at the AUG start codon of the mRNA transcript and scan for AA dinucleotide sequences (see, Elbashir et al. EMBO J. 20: 6877-6888 (2001). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST).

The siRNA can be administered directly or an siRNA expression vectors can be used to induce RNAi can have different design criteria. A vector can have inserted two inverted repeats separated by a short spacer sequence and ending with a string of T's which serve to terminate transcription. The expressed RNA transcript is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) can be suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA. The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Determining the functional effect" refers to assaying for a compound that increases or decreases a parameter that is indirectly or directly under the influence of a polynucleotide or polypeptide of the invention, e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of an substrate; changes in enzymatic activity, e.g., kinase activity, measurement of changes in protein levels of a polypeptide of the invention; measurement of RNA stability; G-protein binding; GPCR phosphorylation or dephosphorylation; signal transduction, e.g., receptor-ligand interactions, second messenger concentrations (e.g., cAMP, IP3, or intracellular Ca2+); identification of downstream or reporter gene expression (CAT, luciferase, β-gal, GFP and the like), e.g., via chemiluminescence, fluorescence, colorimetric reactions, antibody binding, inducible markers, and ligand binding assays.

Samples or assays comprising a nucleic acid or protein disclosed herein that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

"Biological sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e., prostate, lymph node, liver, bone marrow, blood cell), the size and type of the tumor (i.e., solid or suspended (i.e., blood or ascites)), among other factors. Representative biopsy techniques include excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The immunoconjugate can be used for targeting the effector moiety to a N-cadherin positive cell, particularly cells, which express the N-cadherin protein. Such differences can be readily apparent when viewing the bands of gels with approximately similarly loaded with test and controls samples. Examples of cytotoxic agents include, but are not limited to ricin, doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In some embodiments, the invention provides antibodies to N-cadherin. N-cadherin antibodies may be used systemically to treat cancer (e.g., prostate or bladder cancer) alone or when conjugated with an effector moiety. N-cadherin antibodies conjugated with toxic agents, such as ricin, as well as unconjugated antibodies may be useful therapeutic agents naturally targeted to N-cadherin-bearing prostate cancer cells. Such antibodies can be useful in blocking invasiveness. Suitable N-cadherin antibodies for use according to the invention include, but are not limited to, EC4 1H7, 1F12, 2B3, as well as the antibodies disclosed in U.S. Ser. No. 61/113,042 and 61/113,054, herein incorporated by reference in their entirety.

Additionally, the recombinant protein of the invention comprising the antigen-binding region of any of the monoclonal antibodies of the invention can be used to treat cancer. In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, ricin, abrin, glucocorticoid and radioisotopes.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington; The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

Epithelial to Mesenchymal Transition (EMT) refers to the acquisition of stromal features by epithelial tumor cells. In cancer, EMT is associated with invasive and motile behavior and may be central process underlying metastasis. EMT is associated with poor prognosis and is mediated by multiple transcription factors, such as, SNAIL, SLUG and TWIST.

Detailed Embodiments

The present invention provides methods of diagnosis and providing a prognosis for individuals at risk for a cancer that expresses a N-Cadherin protein or mRNA transcript, particularly urogenital cancers including prostate and/or bladder cancer. The methods generally comprise contacting a test tissue sample from an individual at risk of having a cancer that expresses a N-Cadherin protein or mRNA transcript with an antibody that specifically binds to a N-Cadherin protein; and determining the presence or absence of a N-Cadherin protein in the test tissue sample in comparison to a control tissue sample from an individual known to be negative for a cancer that expresses a N-Cadherin protein or mRNA transcript. Typically, the tissue sample is serum, but can also be a tissue from a biopsy, particularly from a urogenital tissue including prostate tissue or bladder tissue. Usually, the antibody is a monoclonal antibody. A positive diagnosis for a cancer that expresses a N-Cadherin protein or mRNA transcript is indicated when a higher level of N-Cadherin protein is detected in a test tissue sample in comparison to a control tissue sample from an individual known not to have cancer, for example, 10%, 20%, 30%, 40%, 50%, 60%, 70%, 80%, 90%, 100%, 2-fold, 3-fold, 4-fold higher or more. The detection methods can be carried out, for example, using standard ELISA techniques known in the art (reviewed in Gosling, *Immunoassays: A Practical Approach*, 2000, Oxford University Press). Detection is accomplished by labeling a primary antibody or a secondary antibody with, for example, a radioactive isotope, a fluorescent label, an enzyme or any other detectable label known in the art.

In another embodiment, invention provides methods of diagnosis and providing a prognosis for individuals at risk for a cancer that expresses a N-Cadherin protein or mRNA transcript, particularly a prostate or bladder cancer, by contacting a test tissue sample from an individual at risk of having a cancer that expresses a N-Cadherin protein or mRNA transcript with a primer set of a first oligonucleotide and a second oligonucleotide that each specifically hybridize to a N-Cadherin nucleic acid; amplifying the N-Cadherin nucleic acid in the sample; and determining the presence or absence of the N-Cadherin nucleic acid in the test tissue sample in comparison to a control tissue sample from an individual known to be negative for a cancer that expresses a N-Cadherin protein or mRNA transcript. Again, usually the tissue sample is serum, but can also be a tissue from a biopsy, particularly a urogenital tissue including a prostate or bladder tissue. A positive diagnosis for a cancer that expresses a N-Cadherin protein or mRNA transcript is indicated when a higher level of N-Cadherin transcribed RNA is detected in a test tissue sample in comparison to a control tissue sample from an individual known not to have cancer.

The invention also provides methods for improving the response to cancer therapy in a cancer that expresses a N-Cadherin protein or mRNA transcript by administering a therapeutically effective amount of a compound that inhibits the binding of N-Cadherin protein to, respectively, a N-Cadherin receptor on a cell of the cancer tumor tissue. In some embodiments the methods of inhibiting N-Cadherin binding to its receptor are carried out concurrently with another anticancer therapy, including, for example, known chemotherapeutics, immunotherapeutics, and radiotherapy for the reversal of resistance, tumor progression, and metastasis.

The present invention further provides methods of inhibiting the growth of and promoting the regression of a tumor that expresses N-Cadherin protein, the methods comprising inhibiting the binding of N-Cadherin protein to, respectively, a N-Cadherin receptor on a cell of the tumor tissue. The methods can be carried out by administering to an individual in need thereof a sufficient amount of a compound that inhibits the binding of a N-Cadherin protein to respectively, a N-Cadherin receptor. In some embodiments, the compound specifically binds to a N-Cadherin protein. In some embodiments, the compound specifically binds to a N-Cadherin receptor. In some embodiments, the compound prevents the transcription or the translation of a N-Cadherin protein. The methods find particular use in treating prostate and bladder cancer. In some embodiments, the compound comprises a polypeptide, including an antibody or an analog or fragment of a N-Cadherin polypeptide.

The methods find particular application in the diagnosis, prognosis and treatment of prostate and bladder cancers. In certain embodiments the methods are applied to hormone refractory or therapy resistant cancers. In certain embodiments the methods are applied to metastatic cancers. For example comparisons of differential expression of a N-Cadherin protein and/or mRNA can be used to determine the stage of cancer of an individual having a cancer that expresses a N-Cadherin protein or mRNA transcript.

Treatment will generally involve the repeated administration of the anti-N-Cadherin antibodies, immunoconjugates, inhibitors, and siRNA preparations via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half life of the agents used, the degree of N-Cadherin expression in the patient, the extent of circulating shed N-Cadherin antigen, the desired steady-state antibody concentration level, frequency of treatment, and the influence of chemotherapeutic agents used in combination with the treatment method of the invention. Typical daily doses may range from about 0.1 to 100 mg/kg. Doses in the range of 10-500 mg of the mAb or immunoconjugates per week may be effective and well tolerated, although even higher weekly doses may be appropriate and/or well tolerated. The principal determining factor in defining the appropriate dose is the amount of a particular agent necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

Direct administration of the agents is also possible and may have advantages in certain contexts. For example, for the treatment of bladder carcinoma, the agents may be injected directly into the bladder. Because agents administered directly to bladder will be cleared from the patient rapidly, it may be possible to use non-human or chimeric antibodies effectively without significant complications of antigenicity.

The invention further provides vaccines formulated to contain a N-Cadherin protein or fragment thereof. The use of a tumor antigen in a vaccine for generating humoral and cell-mediated immunity for use in anti-cancer therapy is well known in the art and, for example, has been employed in prostate cancer using human PSMA and rodent PAP immunogens (Hodge et al., 1995, Int. J. Cancer 63: 231-237; Fong et al., 1997, J. Immunol. 159: 3113-3117). Such methods can be readily practiced by employing a N-Cadherin protein, or fragment thereof, or a N-Cadherin-encoding nucleic acid molecule and recombinant vectors capable of expressing and appropriately presenting the N-Cadherin immunogen.

For example, viral gene delivery systems may be used to deliver a N-Cadherin-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding a N-Cadherin protein or fragment thereof introduced into the patient (e.g., intramuscularly) to induce an anti-tumor response. In one embodiment, the full-length human N-Cadherin cDNA may be employed. In another embodiment, N-Cadherin nucleic acid molecules encoding specific cytotoxic T lymphocyte (CTL) epitopes may be employed. CTL epitopes can be determined using specific algorithms (e.g., Epimer, Brown University) to identify peptides within a N-cadherin protein which are capable of optimally binding to specified HLA alleles.

Various ex vivo strategies may also be employed. One approach involves the use of dendritic cells to present N-Cadherin antigen to a patient's immune system. Dendritic cells express MHC class I and 11, B7 costimulator, and IL-12, and are thus highly specialized antigen presenting cells. In prostate cancer, autologous dendritic cells pulsed with peptides of the N-Cadherin can be used to stimulate prostate cancer patients' immune systems (Tjoa et al., 1996, Prostate 28: 65-69; Murphy et al., 1996, Prostate 29: 371-380). Dendritic cells can be used to present N-Cadherin peptides to T cells in the context of MHC class I and II molecules. In one embodiment, autologous dendritic cells are pulsed with N-Cadherin peptides capable of binding to MHC molecules. In another embodiment, dendritic cells are pulsed with the complete N-Cadherin protein. Yet another embodiment involves engineering the expression of the N-Cadherin gene in dendritic cells using various implementing vectors known in the art, such as adenovirus (Arthur et al., 1997, Cancer Gene Ther. 4: 17-25), retrovirus (Henderson et al., 1996, Cancer Res. 56: 3763-3770), lentivirus, adeno-associated virus, DNA transfection (Ribas et al., 1997, Cancer Res. 57: 2865-2869), and tumor-derived RNA transfection (Ashley et al., 1997, J. Exp. Med. 186: 1177-1182).

Anti-idiotypic anti-N-Cadherin antibodies can also be used in anti-cancer therapy as a vaccine for inducing an immune response to cells expressing a N-Cadherin protein, respectively. Specifically, the generation of anti-idiotypic antibodies is well known in the art and can readily be adapted to generate anti-idiotypic anti-N-Cadherin antibodies that respectively mimic an epitope on a N-Cadherin protein (see, for example, Wagner et al., 1997, Hybridoma 16: 33-40; Foon et al., 1995, J Clin Invest 96: 334-342; Herlyn et al., 1996, Cancer Immunol Immunother 43: 65-76). Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing N-Cadherin. Using the N-Cadherin-encoding DNA molecules described herein, constructs comprising DNA encoding a N-Cadherin protein/immunogen and appropriate regulatory sequences may be injected directly into muscle or skin of an individual, such that the cells of the muscle or skin take-up the construct and express the encoded N-Cadherin protein/immunogen. The N-Cadherin protein/immunogen may be expressed as a cell surface protein or be secreted. Expression of the N-Cadherin protein/immunogen results in the generation of prophylactic or therapeutic humoral and cellular immunity against prostate cancer. Various prophylactic and therapeutic genetic immunization techniques known in the art may be used (for review, see information and references published at internet address www.genweb.com).

The invention further provides methods for inhibiting cellular activity (e.g., cell proliferation, activation, or propagation) of a cell expressing multiple N-Cadherin antigens on its cell surface. This method comprises reacting the immunoconjugates of the invention (e.g., a heterogeneous or homogenous mixture) with the cell so that the N-Cadherin antigens on the cell surface forms a complex with the immunoconjugates. The greater the number of N-Cadherin antigens on the cell surface, the greater the number of N-Cadherin-antibody complexes that can, respectively, be used. The greater the number of N-Cadherin-antibody complexes the greater the cellular activity that is inhibited.

A heterogeneous mixture includes N-Cadherin antibodies that recognize different or the same epitope, each antibody being conjugated to the same or different therapeutic agent. A homogenous mixture includes antibodies that recognize the same epitope, each antibody being conjugated to the same therapeutic agent.

The invention further provides methods for inhibiting the biological activity of N-Cadherin by respectively blocking N-Cadherin from binding its receptor. The methods comprises contacting an amount of N-Cadherin with an antibody or immunoconjugate of the invention under conditions that permit a N-Cadherin-immunoconjugate or N-Cadherin-antibody complex thereby, respectively, blocking N-Cadherin from binding its ligand and inhibiting the activity of N-Cadherin.

In some embodiments, the invention provides a method of treating cancer, particularly a cancer which expresses N-Cadherin, or of inhibiting the growth of a cancer cell expressing a N-Cadherin protein by treating a subject or contacting the cancer cell with an antibody or fragment thereof that recognizes and binds the N-Cadherin protein in an amount effective to inhibit the growth of the cancer cell. In some embodiments, the cancer cell is a prostate cancer cell or a bladder cancer cell. The contacting antibody can be a monoclonal antibody and/or a chimeric antibody. In some embodiments, the chimeric antibody comprises a human immunoglobulin constant region. In some embodiments, the antibody is a human antibody or comprises a human immunoglobulin constant region. In further embodiments, the antibody fragment comprises an Fab, F(ab)$_2$, or Fv. In other embodiments, the fragment comprises a recombinant protein having an antigen-binding region.

In another embodiment, the invention provides methods for treating cancer, particularly a cancer expressing N-Cadherin or selectively inhibiting a cell expressing a N-Cadherin antigen by reacting any one or a combination of the immunoconjugates of the invention with the cell in an amount sufficient to inhibit the cell. Such amounts include an amount to kill the cell or an amount sufficient to inhibit cell growth or proliferation. As discussed supra the dose and dosage regimen will depend on the nature of the disease or disorder to be treated associated with N-Cadherin, its population, the site to which the antibodies are to be directed, the characteristics of the particular immunotoxin, and the patient. For example, the amount of immunoconjugate can be in the range of 0.1 to 200 mg/kg of patient weight. The immunoconjugate can comprise the anti-N-Cadherin antibody or the fragment linked to a therapeutic agent. The therapeutic agent can be cytotoxic agent. The cytotoxic agent can be selected from a group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, and glucocorticoidricin. The therapeutic agent can be a radioactive isotope. The therapeutic isotope can be selected from the group consisting of $^{212}$Bi, $^{131}$I, $^{111}$In, $^{90}$Y and $^{186}$Re.

In any of the embodiments above, a chemotherapeutic drug and/or radiation therapy can be administered further. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally. In some embodiments, the patient has a urogenital cancer (e.g., bladder cancer, prostate cancer). In some embodiments of the above, the patient suffers from prostate cancer and optionally further receives patient hormone ablation therapy. In some embodiments, the contacting comprises administering the antibody directly into the cancer or a metastasis of the cancer.

In some embodiments, the immunoconjugate has a cytotoxic agent which is a small molecule. Toxins such as maytansin, maytansinoids, saporin, gelonin, ricin or calicheamicin and analogs or derivatives thereof are also suitable. Other cytotoxic agents that can be conjugated to the anti-N-Cadherin antibodies include BCNU, streptozoicin, vincristine and 5-fluorouracil. Enzymatically active toxins and fragments thereof can also be used. The radio-effector moieties may be incorporated in the conjugate in known ways (e.g., bifunctional linkers, fusion proteins). The antibodies of the present invention may also be conjugated to an effector moiety which is an enzyme which converts a prodrug to an active chemotherapeutic agent. See, WO 88/07378; U.S. Pat. No. 4,975,278; and U.S. Pat. No. 6,949,245. The antibody or immunoconjugate may optionally be linked to nonprotein polymers (e.g., polyethylene glycol, polypropylene glycol, polyoxyalkylenes, or copolymers of polyethylene glycol and polypropylene glycol).

Conjugates of the antibody and cytotoxic agent may be made using methods well known in the art (see, U.S. Pat. No. 6,949,245). For instance, the conjugates may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used.

Methods of Administration and Formulation

The anti-N-cadherin antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic.

The compositions for administration will commonly comprise an agent as described herein (e.g., N-cadherin inhibitors, N-cadherin antibodies and immunoconjugates, N-cadherin siRNA and vectors thereof) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the antibodies and immunoconjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly(2-hydroxyethyl-methacrylate), or poly(vinylalcohol)), polylactides. The antibodies and immunocongugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention with other cancer therapies (e.g, radical prostatectomy), radiation therapy (external beam or brachytherapy), hormone therapy (e.g., orchiectomy, LHRH-analog therapy to suppress testosterone production, anti-androgen therapy), or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly. Luteinizing hormone-releasing hormone (LHRH) agonists decrease the production of testosterone. These agents may be injected either monthly or longer. Two such analogs are leuprolide and goserelin. Anti-androgens (e.g., flutamide, bicalutamide, and nilutamide) may also be used. Total androgen blockade refers to the use of anti-androgens in combination with orchiectomy or LHRH analogs, the s combination is called. Chemotherapy is an option for patients whose prostate cancer has spread outside of the prostate gland and for whom hormone therapy has failed. It is not expected to destroy all of the cancer cells, but it may slow tumor growth and reduce pain. Some of the chemotherapy drugs used in treating prostate cancer that has returned or continued to grow and spread after treatment with hormonal therapy include doxorubicin (Adriamycin), estramustine, etoposide, mitoxantrone, vinblastine, and paclitaxel. Two or more drugs are often given together to reduce the likelihood of the cancer cells becoming resistant to chemotherapy. Small cell carcinoma is a rare type of prostate cancer that is more likely to respond to chemotherapy than to hormonal therapy.

In some embodiments, a "cardioprotectant" is also administered with the N-cadherin antibody, N-cadherin binding inhibitor, or N-cadherin siRNA molecule for use to according to the invention (see, U.S. Pat. No. 6,949,245). A cardioprotectant is a compound or composition which prevents or reduces myocardial dysfunction (i.e. cardiomyopathy and/or congestive heart failure) associated with administration of a drug, such as an anthracycline antibiotic to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al. The Annals of Pharmacotherapy 28:1063-1072 (1994)); a lipid-lowering agent and/or anti-oxidant such as probucol (Singal et al. J. Mol. Cell Cardiol. 27:1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propyl-phosphoro-thioic acid (WR-151327), see Green et al. Cancer Research 54:738-741 (1994); digoxin (Bristow, M. R. In: Bristow M R, ed. Drug-Induced Heart Disease. New York: Elsevier 191-215 (1980)); beta-blockers such as metoprolol (Hjalmarson et al. Drugs 47:Suppl 4:31-9 (1994); and Shaddy et al. Am. Heart J. 129:197-9 (1995)); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al., Anticancer Res. 13:1607-1612 (1993)); selenoorganic compounds such as P251 (Elbesen); and the like.

The combined administrations contemplates coadministration, using separate formulations or a single pharmaceutical formulation, and consecutive administration in either order, wherein preferably there is a time period while both (or all) active agents simultaneously exert their biological activities.

Molecules and compounds identified that indirectly or directly modulate the expression and/or function of a N-cadherin protein can be useful in treating cancers that, respectively, express N-cadherin. N-cadherin protein modulators can be administered alone or co-administered in combination with conventional chemotherapy, radiotherapy or immunotherapy as well as currently developed therapeutics.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more active N-cadherin protein modulators, optionally in combination with one or more chemotherapeutic agents or immunotherapeutic agents, in a sustained release formulation. Typically, the N-cadherin modulator is administered therapeutically as a sensitizing agent that increases the susceptibility of tumor cells to other cytotoxic cancer therapies, including chemotherapy, radiation therapy, immunotherapy and hormonal therapy.

In therapeutic use for the treatment of cancer, the N-cadherin modulators or inhibitors utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations (e.g., N-cadherin siRNAs, N-cadherin antibodies, N-cadherin vaccines, N-cadherin inhibitors, and immunoconjugates) for use according to the invention are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

Assays for Modulators of N-Cadherin Protein

Modulation of a N-Cadherin protein, and corresponding modulation of cellular, e.g., tumor cell, proliferation, can be assessed using a variety of in vitro and in vivo assays, including cell-based models. Such assays can be used to test for inhibitors and activators of a N-Cadherin protein, and, consequently, inhibitors and activators of cellular proliferation, including modulators of chemotherapeutic sensitivity and toxicity. Such modulators of a N-Cadherin protein are useful for treating disorders related to pathological cell proliferation, e.g., cancer. Modulators of N-Cadherin protein are tested using either recombinant or naturally occurring N-Cadherin, preferably human N-Cadherin.

Measurement of cellular proliferation modulation with a N-Cadherin protein or a cell expressing a N-Cadherin protein, either recombinant or naturally occurring, can be performed using a variety of assays, in vitro, in vivo, and ex vivo, as described herein. A suitable physical, chemical or phenotypic change that affects activity, e.g., enzymatic activity such as kinase activity, cell proliferation, or ligand binding (e.g., a N-Cadherin protein receptor) can be used to assess the influence of a test compound on the polypeptide of this invention. When the functional effects are determined using intact cells or animals, one can also measure a variety of effects, such as, ligand binding, kinase activity, transcriptional changes to both known and uncharacterized genetic markers (e.g., northern blots), changes in cell metabolism, changes related to cellular proliferation, cell surface marker expression, DNA synthesis, marker and dye dilution assays (e.g., GFP and cell tracker assays), contact inhibition, tumor growth in nude mice, etc.

In Vitro Assays

Assays to identify compounds with N-Cadherin modulating activity can be performed in vitro. Such assays can use a full length N-Cadherin protein or a variant thereof, or a mutant thereof; or a fragment of a N-Cadherin protein. Purified recombinant or naturally occurring N-Cadherin protein can be used in the in vitro methods of the invention. In addition to purified N-Cadherin protein, the recombinant or naturally occurring N-Cadherin protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein. Other in vitro assays include enzymatic activity assays, such as phosphorylation or autophosphorylation assays).

In one embodiment, a high throughput binding assay is performed in which the N-Cadherin protein or a fragment thereof is contacted with a potential modulator and incubated for a suitable amount of time. In one embodiment, the potential modulator is bound to a solid support, and the N-Cadherin protein is added. In another embodiment, the N-Cadherin protein is bound to a solid support. A wide variety of modulators can be used, as described below, including small organic molecules, peptides, antibodies, and N-Cadherin ligand analogs. A wide variety of assays can be used to identify N-Cadherin-modulator binding, including labeled protein-protein binding assays, electrophoretic mobility shifts, immunoassays, enzymatic assays such as kinase assays, and the like. In some cases, the binding of the candidate modulator is determined through the use of competitive binding assays, where interference with binding of a known ligand or substrate is measured in the presence of a potential modulator.

In one embodiment, microtiter plates are first coated with either a N-Cadherin protein or a N-Cadherin protein receptor, and then exposed to one or more test compounds potentially capable of inhibiting the binding of a N-Cadherin protein to a N-Cadherin protein receptor. A labeled (i.e., fluorescent, enzymatic, radioactive isotope) binding partner of the coated protein, either a N-Cadherin protein receptor or a N-Cadherin protein, is then exposed to the coated protein and test compounds. Unbound protein is washed away as necessary in between exposures to a N-Cadherin protein, a N-Cadherin protein receptor, or a test compound. An absence of detectable signal indicates that the test compound inhibited the binding interaction between a N-Cadherin protein and, respectively, a N-Cadherin protein receptor. The presence of detectable signal (i.e., fluorescence, colorimetric, radioactivity) indicates that the test compound did not inhibit the binding interaction between a N-Cadherin protein and, respectively, a N-Cadherin protein receptor. The presence or absence of detectable signal is compared to a control sample that was not exposed to a test compound, which exhibits uninhibited signal. In some embodiments the binding partner is unlabeled, but exposed to a labeled antibody that specifically binds the binding partner.

Cell-Based In Vivo Assays

In another embodiment, N-Cadherin protein is expressed in a cell, and functional, e.g., physical and chemical or phenotypic, changes are assayed to identify N-Cadherin and modulators of cellular proliferation, e.g., tumor cell proliferation. Cells expressing N-Cadherin proteins can also be used in binding assays and enzymatic assays. Any suitable functional effect can be measured, as described herein. For example, cellular morphology (e.g., cell volume, nuclear volume, cell perimeter, and nuclear perimeter), ligand binding, kinase activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoechst dye with FACS analysis), are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), Hela (cervical), PC3 (prostate, p53 mutant), MDA-MB-231 (breast, p53 wild-type). Cancer cell lines can be p53 mutant, p53 null, or express wild type p53. The N-Cadherin protein can be naturally occurring or recombinant. Also, fragments of N-Cadherin or chimeric N-Cadherin proteins can be used in cell based assays.

Cellular N-Cadherin polypeptide levels can be determined by measuring the level of protein or mRNA. The level of N-Cadherin protein or proteins related to N-Cadherin are measured using immunoassays such as western blotting, ELISA and the like with an antibody that selectively binds, respectively, to the N-Cadherin polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, N-Cadherin expression can be measured using a reporter gene system. Such a system can be devised using an N-Cadherin protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

Animal Models

Animal models of cellular proliferation also find use in screening for modulators of cellular proliferation. Similarly, transgenic animal technology including gene knockout technology, for example as a result of homologous recombination with an appropriate gene targeting vector, or gene overexpression, will result in the absence or increased expression of the N-Cadherin protein. The same technology can also be applied to make knock-out cells. When desired, tissue-specific expression or knockout of the N-Cadherin protein may be necessary. Transgenic animals generated by such methods find use as animal models of cellular proliferation and are additionally useful in screening for modulators of cellular proliferation.

Knock-out cells and transgenic mice can be made by insertion of a marker gene or other heterologous gene into an endogenous N-Cadherin gene site in the mouse genome via homologous recombination. Such mice can also be made by substituting an endogenous N-Cadherin, respectively, with a mutated version of the N-Cadherin gene, or by, respectively, mutating an endogenous N-Cadherin, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988), *Teratocarcinomas and Embryonic Stem Cells: A Practical Approach*, Robertson, ed., IRL Press, Washington, D.C., (1987), and Pinkert, *Transgenic Animal Technology: A Laboratory Handbook*, Academic Press (2003).

Exemplary Assays

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify N-Cadherin modulators. Typically, transformed host cells (e.g., cells that grow on soft agar) are used in this assay. For example, RKO or HCT116 cell lines can be used. Techniques for soft agar growth or colony formation in suspension assays are described in Freshney, *Culture of Animal Cells a Manual of Basic Technique*, 3$^{rd}$ ed., Wiley-Liss, New York (1994), herein incorporated by reference. See also, the methods section of Garkavtsev et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when contacted with cellular proliferation modulators, regenerate a normal phenotype and become contact inhibited and would grow to a lower density.

Contact inhibition and density limitation of growth assays can be used to identify N-Cadherin modulators which are capable of inhibiting abnormal proliferation and transformation in host cells. Typically, transformed host cells (e.g., cells that are not contact inhibited) are used in this assay. For example, RKO or HCT116 cell lines can be used. In this assay, labeling index with [$^3$H]-thymidine at saturation density is a preferred method of measuring density limitation of growth. Transformed host cells are contacted with a potential N-cadherin modulator and are grown for 24 hours at saturation density in non-limiting medium conditions. The percentage of cells labeling with [$^3$H]-thymidine is determined autoradiographically. See, Freshney (1994), supra. The host cells contacted with a N-cadherin modulator would give arise to a lower labeling index compared to control (e.g., transformed host cells transfected with a vector lacking an insert).

Growth Factor or Serum Dependence

Growth factor or serum dependence can be used as an assay to identify N-cadherin modulators. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When transformed cells are contacted with a N-Cadherin modulator, the cells would reacquire serum dependence and would release growth factors at a lower level.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mihich (ed.): "Biological Responses in Cancer." New York, Academic Press, pp. 178-184 (1985)). Similarly, tumor angiogenesis factor (TAF) is released at a higher level in tumor cells than their normal counterparts. See, e.g., Folkman, Angiogenesis and cancer, *Sem Cancer Biol.* (1992)).

Tumor specific markers can be assayed to identify N-Cadherin modulators which decrease the level of release of these markers from host cells. Typically, transformed or tumorigenic host cells are used. Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305-312 (1980); Gulino, *Angiogenesis, tumor vascularization, and potential interference with tumor growth*. In Mihich, E. (ed): "Biological Responses in Cancer." New York, Plenum (1985); *Freshney Anticancer Res.* 5:111-130 (1985).

Invasiveness into Matrigel

The degree of invasiveness into Matrigel or some other extracellular matrix constituent can be used as an assay to identify N-Cadherin modulators which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Therefore, N-Cadherin modulators can be identified by measuring changes in the level of invasiveness between the host cells before and after the introduction of potential modulators. If a compound modulates N-Cadherin, its expression in tumorigenic host cells would affect invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Tumor Growth In Vivo

Effects of N-Cadherin modulators on cell growth can be tested in transgenic or immune-suppressed mice. Knock-out transgenic mice can be made, in which the endogenous N-Cadherin gene is disrupted. Such knock-out mice can be used to study effects of N-Cadherin, e.g., as a cancer model, as a means of assaying in vivo for compounds that modulate N-Cadherin, and to test the effects of restoring a wild-type or mutant N-Cadherin to a knock-out mouse.

Knock-out cells and transgenic mice can be made by insertion of a marker gene or other heterologous gene into the endogenous N-Cadherin gene site in the mouse genome via homologous recombination. Such mice can also be made by substituting the endogenous N-Cadherin with a mutated version of N-Cadherin, or by mutating the endogenous N-Cadherin, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987). These knock-out mice can be used as hosts to test the effects of various N-Cadherin modulators on cell growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. Hosts are treated with N-Cadherin modulators, e.g., by injection. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, N-Cadherin modulators which are capable, e.g., of inhibiting abnormal cell proliferation can be identified.

Screening Methods

The present invention also provides methods of identifying compounds that inhibit the binding of a N-Cadherin protein, respectively, to a N-Cadherin receptor, wherein said compounds find use in inhibiting the growth of and promoting the regression of a tumor that expresses N-Cadherin protein, for example a urogenital cancer tumor, including a prostate or bladder cancer tumor.

Using the assays described herein, one can identify lead compounds that are suitable for further testing to identify those that are therapeutically effective modulating agents by screening a variety of compounds and mixtures of compounds for their ability to decrease, inhibit the binding of a N-Cadherin protein, respectively, to a N-Cadherin receptor. Compounds of interest can be either synthetic or naturally occurring.

Screening assays can be carried out in vitro or in vivo. Typically, initial screening assays are carried out in vitro, and can be confirmed in vivo using cell based assays or animal models. For instance, proteins of the regenerating gene family are involved with cell proliferation. Therefore, compounds that inhibit the binding of a N-Cadherin protein, respectively, to a N-Cadherin receptor can inhibit cell proliferation resulting from this binding interaction in comparison to cells unexposed to a test compound. Also, the binding of a N-Cadherin protein, respectively, to a N-Cadherin receptor is involved with tissue injury responses, inflammation, and dysplasia. In animal models, compounds that inhibit the binding of a N-Cadherin protein, respectively, to its receptor can, for example, inhibit wound healing or the progression of dysplasia in comparison to an animal unexposed to a test compound. See, for example, Zhang, et al., *World J Gastroenter* (2003) 9:2635-41.

Usually a compound that inhibits the binding of N-Cadherin, respectively, to a N-cadherin receptor is synthetic. The screening methods are designed to screen large chemical libraries by automating the assay steps and providing compounds from any convenient source to assays, which are typically run in parallel (e.g., in microtiter formats on microtiter plates in robotic assays).

The invention provides in vitro assays for inhibiting N-Cadherin binding to its receptor in a high throughput format. For each of the assay formats described, "no modulator" control reactions which do not include a modulator provide a background level of N-Cadherin binding interaction to its receptor or receptors. In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (96) modulators. If 1536 well plates are used, then a single plate can easily assay from about 100-about 1500 different compounds. It is possible to assay many different plates per day; assay screens for up to about 6,000-20,000, and even up to about 100,000-1,000,000 different compounds is possible using the integrated systems of the invention. The steps of labeling, addition of reagents, fluid changes, and detection are compatible with full automation, for instance using programmable robotic systems or "integrated systems" commercially available, for example, through BioTX Automation, Conroe, Tex.; Qiagen, Valencia, Calif.; Beckman Coulter, Fullerton, Calif.; and Caliper Life Sciences, Hopkinton, Mass.

Essentially any chemical compound can be tested as a potential inhibitor of N-Cadherin binding to its receptor for use in the methods of the invention. Most preferred are generally compounds that can be dissolved in aqueous or organic (especially DMSO-based) solutions are used. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland), as well as providers of small organic molecule and peptide libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), and Tripos, Inc. (St. Louis, Mo.).

In one preferred embodiment, inhibitors of the N-Cadherin receptor binding interaction are identified by screening a combinatorial library containing a large number of potential therapeutic compounds (potential modulator compounds). Such "combinatorial chemical or peptide libraries" can be screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.).

siRNA Technology

The design and making of siRNA molecules and vectors are well known to those of ordinary skill in the art. For instance, an efficient process for designing a suitable siRNA is to start at the AUG start codon of the mRNA transcript and scan for AA dinucleotide sequences (see, Elbashir et al. EMBO J. 20: 6877-6888 (2001). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST.

The siRNA expression vectors to induce RNAi can have different design criteria. A vector can have inserted two inverted repeats separated by a short spacer sequence and ending with a string of T's which serve to terminate transcription. The expressed RNA transcript is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hair siRNAs with these various stem lengths (e.g., 15 to 30) can be suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA. These control elements may be designed to allow the clinician to turn off or on the expression of the gene by adding or controlling external factors to which the regulatory elements are responsive.

In some embodiments, the invention provides a method for inhibiting the growth of a cancer cell expressing a N-Cadherin protein by contacting the cancer cell with an antibody or fragment thereof that recognized and binds the protein in an amount effective to inhibit the growth of the cancer cell. In some embodiments, the cancer cell is a prostate cancer cell or a bladder cancer cell. The contacting antibody can be a monoclonal antibody and/or a chimeric antibody. In some embodiments, the chimeric antibody comprises a human immunoglobulin constant region. In some embodiments, the antibody is a human antibody or comprises a human immunoglobulin constant region. In further embodiments, the antibody fragment comprises an Fab, F(ab)$_2$, or Fv. In other embodiments, the fragment comprises a recombinant protein having an antigen-binding region. In yet other embodiments, the antibody or the fragment is an immunoconjugate comprising the antibody or the fragment linked to a therapeutic agent. The therapeutic agent can be cytotoxic agent. The cytotoxic agent can be selected from a group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, and glucocorticoidricin. The therapeutic agent can be a radioactive isotope. The therapeutic isotope can be selected from the group consisting of $^{212}$Bi, $^{131}$I, $^{111}$In, $^{90}$Y and $^{186}$Re. In any of the embodiments above, a chemotherapeutic drug and/or radiation therapy can be administered further. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally. In some embodiments, the patient has a urogenital cancer (e.g., bladder cancer, prostate cancer). In some embodiments of the above, the patient suffers from prostate cancer and optionally further receives patient hormone ablation therapy. In some embodiments, the contacting comprises administering the antibody directly into the cancer or a metastasis of the cancer.

In some embodiments, the immunoconjugate has a cytotoxic agent which is a small molecule. Toxins such as maytansin, maytansinoids, saporin, gelonin, ricin or calicheamicin and analogs or derivatives thereof are also suitable. Other cytotoxic agents that can be conjugated to the N-cadherin antibodies include BCNU, streptozoicin, vincristine and 5-fluorouracil. Enzymatically active toxins and fragments thereof can also be used. The radio- or other labels may be incorporated in the conjugate in known ways (e.g., bifunctional linkers, fusion proteins). The antibodies of the present invention may also be conjugated to an enzyme which converts a prodrug to an active chemotherapeutic agent. See, WO 88/07378 and U.S. Pat. No. 4,975,278. The antibody or immunoconjugate may optionally be linked to nonprotein polymers (e.g., polyethylene glycol, polypropylene glycol, polyoxyalkylenes, or copolymers of polyethylene glycol and polypropylene glycol).

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration may provide from about 0.1 to 100 mg per patient per day. Dosages from 0.1 up to about 100 mg per patient per day may be used. Substantially higher dosages are possible in topical administration. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the antibodies and immunoconjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpylloli-done; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly(2-hydroxyethyl-methacrylate), or poly(vinylalcohol)), polylactides. The antibodies and immunocongugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions containing the inhibitors and agents of the invention (e.g., antibodies) can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, inhibitors of Wnt signaling may also be used to target or sensitize a cell to other cancer therapeutic agents such as 5FU, vinblastine, actinomycin D, cisplatin, methotrexate, and the like. In other embodiments, the methods of the invention can be used with radiation therapy and the like.

EXAMPLES

The following examples are offered to illustrate, but not limit the claimed invention.

Example 1

The data in FIG. 1 show that even though N-cadherin is expressed in only a small subset of the androgen independent cells, that treatment with antibody is sufficient to delay to growth and progression of the androgen independent tumors (pink and yellow curves). These data suggest that the N-cadherin population of cells is required for androgen independent tumor formation, and that blocking it is sufficient to delay tumor progression. These data are consistent with an interpretation that N-cadherin marks a population of androgen independent stem cells. Blocking growth of the stem cells is enough to block growth of the tumor. These data also show that antibodies may work on cells that express normal or even low levels of N-cadherin.

Figure 2:
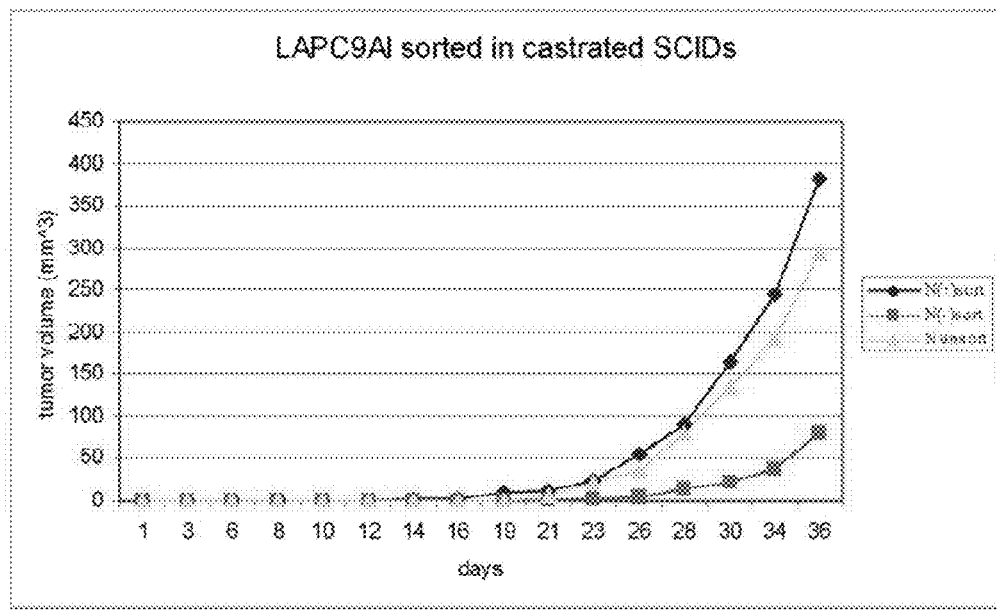
FIG. 2. N-cadherin positive and negative cells were sorted, yielding a population of cells that were 100% and 0% positive for N-cadherin, respectively.

As shown in FIG. 2, cells were injected into castrate mice, and the N-cadherin positive cells formed tumors more quickly and efficiently than the negative population, suggesting that N-cadherin positive cells are either have a growth advantage, or that they have stem cell characteristics and are more tumorigenic than the negative population. Unsorted cells grow similar to the N-cadherin positive cells.

Figure 3:
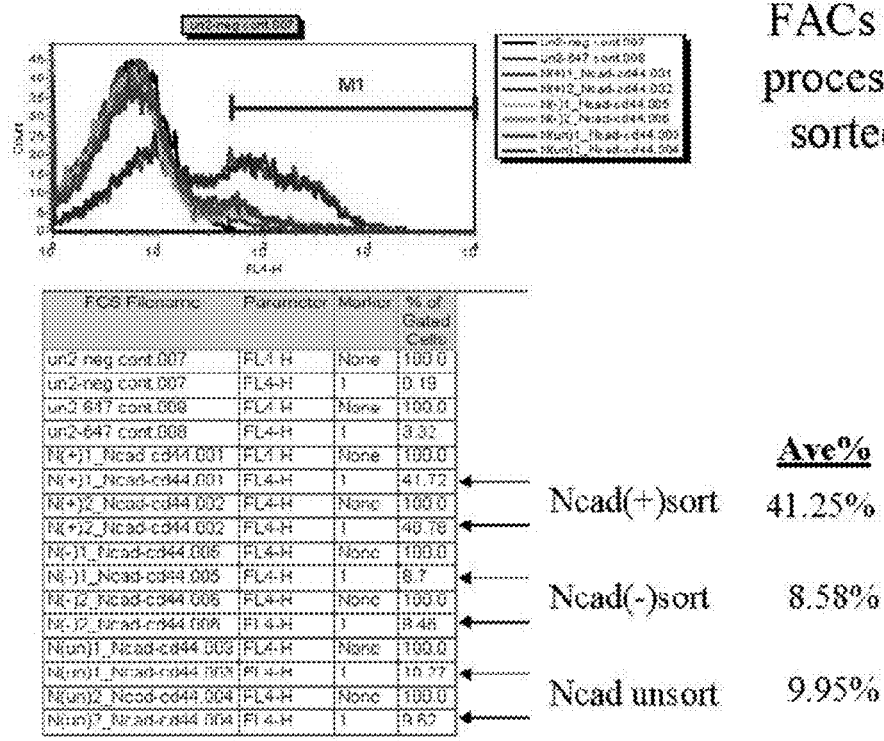
FIGS. 3 and 4. FACS analysis of tumors that grew from purely N-cadherin positive and negative cells, vs the control unsorted population.
Figure 4:
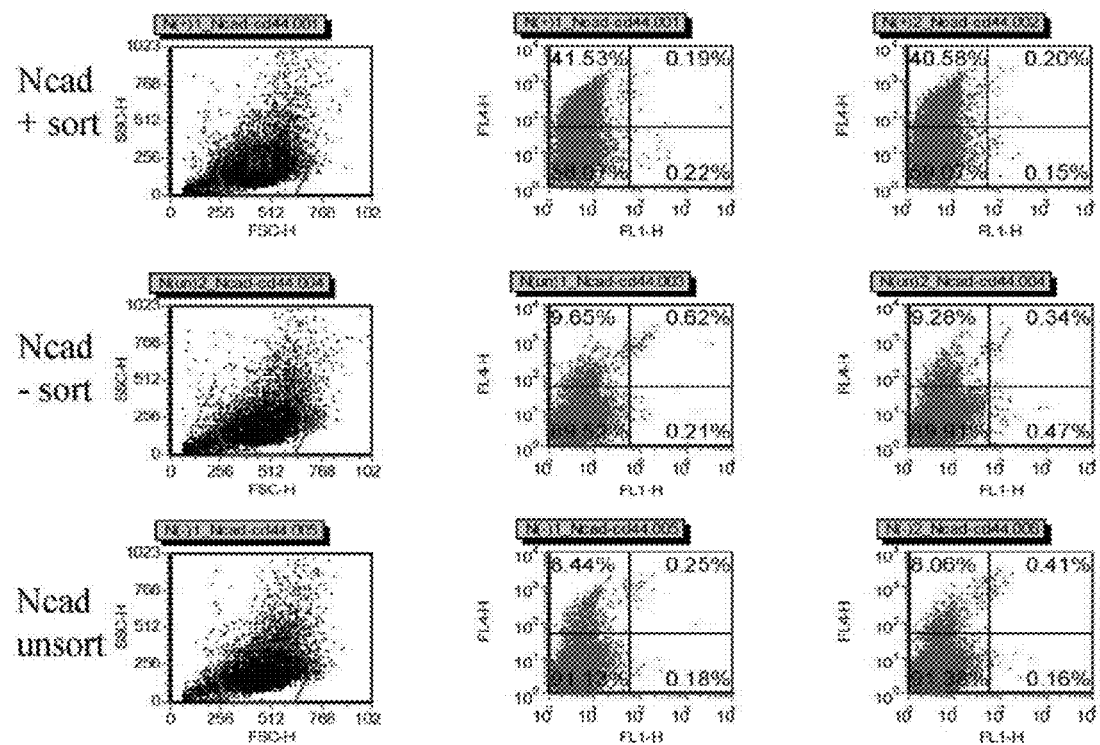

As shown in FIGS. 3 and 4, tumors from 100% N-cad positive cells are only 41.25% positive for N-cadherin, suggesting that these cells give rise to N-cadherin null cells. This is consistent with the hypothesis that N-cadherin positive cells are stem cells that can give rise to more differentiated, N-cadherin negative cells. Meanwhile, the N-cadherin negative population gives rise to tumors that are 9% N-cadherin positive, similar to the unsorted cells. This suggests that growth of these cells requires that a stem-like population acquire or upregulated N-cadherin in order to form androgen independent tumors. The delay in tumorigenicity is caused by the requirement for N-cadherin to give rise to androgen independent tumors.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a cancer patient, comprising the steps of:
   (a) obtaining a test tissue sample from an individual at risk of having a cancer that expresses a N-cadherin protein wherein the N-cadherin comprises the sequence of SEQ ID NO: 1 or SEQ ID NO: 3, wherein the test tissue sample comprises cancer cells;
   (b) detecting an increased expression of N-cadherin of SEQ ID NO: 1 or SEQ ID NO: 3 in a cancer cell in the test tissue sample in comparison to a control tissue sample from an individual known to be negative for the cancer; thereby diagnosing said cancer that expresses a N-cadherin protein; and
   (c) administering an effective amount of an antibody or an antigen-binding fragment thereof that binds domain IV of N-cadherin protein, where the N-cadherin comprises the sequence of SEQ ID NO: 1 or SEQ ID NO: 3 to the individual.

2. The method of claim 1, wherein said tissue sample is prostate or bladder tissue.

3. The method of claim 1, wherein said cancer is a prostate cancer.

4. The method of claim 1, wherein said cancer is a bladder cancer.

5. The method of claim 1, wherein said cancer is a hormone refractory prostate cancer.

6. The method of claim 1, wherein said cancer is a metastatic cancer.

7. The method of claim 1, wherein said antibody is a monoclonal antibody.

8. The method of claim 1, wherein the fragment is a scFv.

9. The method of claim 1, wherein the fragment is a diabody.

10. The method of claim 1, wherein said antibody blocks hormone refractory prostate cancer.

11. The method of claim 1, wherein said antibody blocks cancer stem cells.

* * * * *

SEQUENCE LISTING

<160> NUMBER OF SEQ ID NOS: 4

<210> SEQ ID NO 1
<211> LENGTH: 905
<212> TYPE: PRT
<213> ORGANISM: Homo sapiens
<220> FEATURE:
<223> OTHER INFORMATION: human N-cadherin

<400> SEQUENCE: 1

Met Cys Arg Ile Ala Gly Ala Leu Arg Thr Leu Pro Leu Leu Ala Ala
 1               5                  10                  15

Leu Leu Gln Ala Ser Val Glu Ala Ser Gly Glu Ile Ala Leu Cys Lys
            20                  25                  30

Thr Gly Phe Pro Glu Asp Val Tyr Ser Ala Val Leu Ser Lys Asp Val
        35                  40                  45

His Glu Gly Gln Pro Leu Leu Asn Val Lys Phe Ser Asn Cys Asn Gly
    50                  55                  60

Lys Arg Lys Val Gln Tyr Glu Ser Ser Glu Pro Ala Asp Phe Lys Val
65                  70                  75                  80

Asp Glu Asp Gly Met Val Tyr Ala Val Arg Ser Phe Pro Leu Ser Ser
                85                  90                  95

Glu His Ala Lys Phe Leu Ile Tyr Ala Gln Asp Lys Glu Thr Gln Glu
            100                 105                 110

Lys Trp Gln Val Ala Val Lys Leu Ser Leu Lys Pro Thr Leu Thr Glu
        115                 120                 125

Glu Ser Val Lys Glu Ser Ala Glu Val Glu Glu Ile Val Phe Pro Arg
    130                 135                 140

Gln Phe Ser Lys His Ser Gly His Leu Gln Arg Gln Lys Arg Asp Trp
145                 150                 155                 160

Val Ile Pro Pro Ile Asn Leu Pro Glu Asn Ser Arg Gly Pro Phe Pro
                165                 170                 175

Gln Glu Leu Val Arg Ile Arg Ser Asp Arg Asp Lys Asn Leu Ser Leu
            180                 185                 190

Arg Tyr Ser Val Thr Gly Pro Gly Ala Asp Gln Pro Pro Thr Gly Ile
        195                 200                 205

Phe Ile Ile Asn Pro Ile Ser Gly Gln Leu Ser Val Thr Lys Pro Leu
    210                 215                 220

Asp Arg Glu Gln Ile Ala Arg Phe His Leu Arg Ala His Ala Val Asp
225                 230                 235                 240

Ile Asn Gly Asn Gln Val Glu Asn Pro Ile Asp Ile Val Ile Asn Val
                245                 250                 255

Ile Asp Met Asn Asp Asn Arg Pro Glu Phe Leu His Gln Val Trp Asn
            260                 265                 270

Gly Thr Val Pro Glu Gly Ser Lys Pro Gly Thr Tyr Val Met Thr Val
        275                 280                 285

Thr Ala Ile Asp Ala Asp Asp Pro Asn Ala Leu Asn Gly Met Leu Arg
    290                 295                 300

Tyr Arg Ile Val Ser Gln Ala Pro Ser Thr Pro Ser Pro Asn Met Phe
305                 310                 315                 320

Thr Ile Asn Asn Glu Thr Gly Asp Ile Ile Thr Val Ala Ala Gly Leu
                325                 330                 335

Asp Arg Glu Lys Val Gln Gln Tyr Thr Leu Ile Ile Gln Ala Thr Asp
            340                 345                 350

Met Glu Gly Asn Pro Thr Tyr Gly Leu Ser Asn Thr Ala Thr Ala Val

```
                355                 360                 365
Ile Thr Val Thr Asp Val Asn Asp Asn Pro Pro Glu Phe Thr Ala Met
370                 375                 380
Thr Phe Tyr Gly Glu Val Pro Glu Asn Arg Val Asp Ile Ile Val Ala
385                 390                 395                 400
Asn Leu Thr Val Thr Asp Lys Asp Gln Pro His Thr Pro Ala Trp Asn
                405                 410                 415
Ala Val Tyr Arg Ile Ser Gly Asp Pro Thr Gly Arg Phe Ala Ile
                420                 425                 430
Gln Thr Asp Pro Asn Ser Asn Asp Gly Leu Val Thr Val Lys Pro
                435                 440                 445
Ile Asp Phe Glu Thr Asn Arg Met Phe Val Leu Thr Val Ala Ala Glu
450                 455                 460
Asn Gln Val Pro Leu Ala Lys Gly Ile Gln His Pro Pro Gln Ser Thr
465                 470                 475                 480
Ala Thr Val Ser Val Thr Val Ile Asp Val Asn Glu Asn Pro Tyr Phe
                485                 490                 495
Ala Pro Asn Pro Lys Ile Ile Arg Gln Glu Gly Leu His Ala Gly
                500                 505                 510
Thr Met Leu Thr Thr Phe Thr Ala Gln Asp Pro Asp Arg Tyr Met Gln
                515                 520                 525
Gln Asn Ile Arg Tyr Thr Lys Leu Ser Asp Pro Ala Asn Trp Leu Lys
                530                 535                 540
Ile Asp Pro Val Asn Gly Gln Ile Thr Thr Ile Ala Val Leu Asp Arg
545                 550                 555                 560
Glu Ser Pro Asn Val Lys Asn Asn Ile Tyr Asn Ala Thr Phe Leu Ala
                565                 570                 575
Ser Asp Asn Gly Ile Pro Pro Met Ser Gly Thr Gly Thr Leu Gln Ile
                580                 585                 590
Tyr Leu Leu Asp Ile Asn Asp Asn Ala Pro Gln Val Leu Pro Gln Glu
                595                 600                 605
Ala Glu Thr Cys Glu Thr Pro Asp Pro Asn Ser Ile Asn Ile Thr Ala
                610                 615                 620
Leu Asp Tyr Asp Ile Asp Pro Asn Ala Gly Pro Phe Ala Phe Asp Leu
625                 630                 635                 640
Pro Leu Ser Pro Val Thr Ile Lys Arg Asn Trp Thr Ile Thr Arg Leu
                645                 650                 655
Asn Gly Asp Phe Ala Gln Leu Asn Leu Lys Ile Lys Phe Leu Glu Ala
                660                 665                 670
Gly Ile Tyr Glu Val Pro Ile Ile Ile Thr Asp Ser Gly Asn Pro Pro
                675                 680                 685
Lys Ser Asn Ile Ser Ile Leu Arg Val Lys Val Cys Gln Cys Asp Ser
                690                 695                 700
Asn Gly Asp Cys Thr Asp Val Asp Arg Ile Val Gly Ala Gly Leu Gly
                705                 710                 715                 720
Thr Gly Ala Ile Ile Ala Ile Leu Leu Cys Ile Ile Ile Leu Leu Ile
                725                 730                 735
Leu Val Leu Met Phe Val Val Trp Met Lys Arg Arg Asp Lys Glu Arg
                740                 745                 750
Gln Ala Lys Gln Leu Leu Ile Asp Pro Glu Asp Asp Val Arg Asp Asn
                755                 760                 765
Ile Leu Lys Tyr Asp Glu Glu Gly Gly Gly Glu Glu Asp Gln Asp Tyr
                770                 775                 780
```

```
Asp Leu Ser Gln Leu Gln Gln Pro Asp Thr Val Glu Pro Asp Ala Ile
785                 790                 795                 800

Lys Pro Val Gly Ile Arg Arg Met Asp Glu Arg Pro Ile His Ala Glu
            805                 810                 815

Pro Gln Tyr Pro Val Arg Ser Ala Ala Pro His Pro Gly Asp Ile Gly
        820                 825                 830

Asp Phe Ile Asn Glu Gly Leu Lys Ala Ala Asp Asn Asp Pro Thr Ala
        835                 840                 845

Pro Pro Tyr Asp Ser Leu Leu Val Phe Asp Tyr Glu Gly Ser Gly Ser
    850                 855                 860

Thr Leu Gly Ser Leu Ser Ser Leu Asn Ser Ser Ser Gly Gly Glu
865                 870                 875                 880

Gln Asp Tyr Asp Tyr Leu Asn Asp Trp Gly Pro Arg Phe Lys Lys Leu
            885                 890                 895

Ala Asp Met Tyr Gly Gly Gly Asp Asp
            900                 905

<210> SEQ ID NO 2
<211> LENGTH: 2718
<212> TYPE: DNA
<213> ORGANISM: Homo sapiens
<220> FEATURE:
<223> OTHER INFORMATION: human N-cadherin cDNA
<220> FEATURE:
<221> NAME/KEY: CDS
<222> LOCATION: (1)..(2718)
<223> OTHER INFORMATION: N-cadherin

<400> SEQUENCE: 2
atgtgccgga tagcgggagc gctgcggacc ctgccgctgc tggcggccct gcttcaggcg      60
tctgtagagg cttctggtga atcgcatta  tgcaagactg gatttcctga agatgtttac     120
agtgcagtct tatcgaagga tgtgcatgaa ggacagcctc ttctcaatgt gaagtttagc     180
aactgcaatg gaaaagaaa  agtacaatat gagagcagtg agcctgcaga ttttaaggtg     240
gatgaagatg gcatggtgta tgccgtgaga agctttccac tctcttctga gcatgccaag     300
ttcctgatat atgcccaaga caagagacc  caggaaaagt ggcaagtggc agtaaaattg     360
agcctgaagc caaccttaac tgaggagtca gtgaaggagt cagcagaagt tgaagaaata     420
gtgttcccaa gacaattcag taagcacagt ggccacctac aaaggcagaa gagagactgg     480
gtcatccctc aatcaacttt gccagaaaac tccaggggac ttttcctca  agagcttgtc     540 aggatcaggt ctgatagaga taaaaacctt tcactgcgt  acagtgtaac tgggccagga     600
gctgaccagc ctccaactgg tatcttcatt atcaaccca  tctcgggtca gctgtcggtg     660
acaaagcccc tggatcgcga gcagatagcc cggtttcatt tgagggcaca tgcagtagat     720
attaatggaa atcaagtgga gaaccccatt gacattgtca tcaatgttat tgacatgaat     780
gacaacagac tgagttctt  acaccaggtt tggaatggga cagttcctga gggatcaaag     840
cctggaacat atgtgatgac cgtaacagca attgatgctg acgatccaa  tgccctcaat     900 gggatgttga ggtacagaat cgtgtctcag gctccaagca ccccttcacc caacatgttt     960
acaatcaaca atgagactgg tgacatcatc acagtggcag ctggacttga tcgagaaaaa    1020
gtgcaacagt atacgttaat aattcaagct acagacatgg aaggcaatcc cacatatggc    1080
ctttcaaaca cagccacggc cgtcatcaca gtgacagatg tcaatgacaa tcctccagag    1140
tttactgcca tgacgttta  tggtgaagtt cctgagaaca gggtagacat catagtagct    1200
```

```
aatctaactg tgaccgataa ggatcaaccc catacaccag cctggaacgc agtgtacaga    1260
atcagtggcg gagatcctac tggacggttc gccatccaga ccgacccaaa cagcaacgac    1320
gggttagtca ccgtggtcaa accaatcgac tttgaaacaa ataggatgtt tgtccttact    1380
gttgctgcag aaaatcaagt gccattagcc aagggaattc agcacccgcc tcagtcaact    1440
gcaaccgtgt ctgttacagt tattgacgta aatgaaaacc cttattttgc ccccaatcct    1500
aagatcattc gccaagaaga agggcttcat gccggtacca tgttgacaac attcactgct    1560
caggacccag atcgatatat gcagcaaaat attagataca ctaaattatc tgatcctgcc    1620
aattggctaa aaatagatcc tgtgaatgga caaataacta caattgctgt tttggaccga    1680
gaatcaccaa atgtgaaaaa caatatatat aatgctactt tccttgcttc tgacaatgga    1740
attcctccta tgagtggaac aggaacgctg cagatctatt tacttgatat taatgacaat    1800 gccccctcaag tgttacctca agaggcagag acttgcgaaa ctccagaccc caattcaatt    1860
aatattacag cacttgatta tgacattgat ccaaatgctg gaccatttgc ttttgatctt    1920
cctttatctc cagtgactat taagagaaat tggaccatca ctcggcttaa tggtgatttt    1980
gctcagctta atttaaagat aaaatttctt gaagctggta tctatgaagt tcccatcata    2040
atcacagatt cgggtaatcc tcccaaatca aatatttcca tcctgcgcgt gaaggtttgc    2100
cagtgtgact ccaacgggga ctgcacagat gtggacagga ttgtgggtgc ggggcttggc    2160
accggtgcca tcattgccat cctgctctgc atcatcatcc tgcttatcct tgtgctgatg    2220
tttgtggtat ggatgaaacg gcgggataaa gaacgccagg ccaaacaact tttaattgat    2280
ccagaagatg atgtaagaga taatatttta aaatatgatg aagaaggtgg aggagaagaa    2340
gaccaggact atgacttgag ccagctgcag cagcctgaca ctgtggagcc tgatgccatc    2400
aagcctgtgg gaatccgacg aatggatgaa agacccatcc acgctgagcc ccagtatccg    2460
gtccgatctg cagccccaca ccctggagac attggggact tcattaatga gggccttaaa    2520
gcggctgaca tgaccccac agctccacca tatgactccc tgttagtgtt tgactatgaa    2580
ggcagtggct ccaccttggg gtccttgagc tcccttaatt cctcaagtag tggtggtgag    2640
caggactatg attacctgaa cgactggggg ccacggttca gaaacttgc tgacatgtat    2700 ggtggaggtg atgactga                                                  2718
```

<210> SEQ ID NO 3
<211> LENGTH: 906
<212> TYPE: PRT
<213> ORGANISM: Homo sapiens
<220> FEATURE:
<223> OTHER INFORMATION: human N-cadherin variant, cadherin 2, type 1
      (CDH2), neuronal N-cadherin

<400> SEQUENCE: 3

Met Cys Arg Ile Ala Gly Ala Leu Arg Thr Leu Leu Pro Leu Leu Ala
 1               5                  10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser

```
                85                  90                  95
Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Ile Val Phe Pro
    130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
            180                 185                 190

Leu Arg Tyr Ser Val Thr Gly Pro Gly Ala Asp Gln Pro Pro Thr Gly
        195                 200                 205

Ile Phe Ile Ile Asn Pro Ile Ser Gly Gln Leu Ser Val Thr Lys Pro
    210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
            260                 265                 270

Asn Gly Thr Val Pro Glu Gly Ser Lys Pro Gly Thr Tyr Val Met Thr
        275                 280                 285

Val Thr Ala Ile Asp Ala Asp Asp Pro Asn Ala Leu Asn Gly Met Leu
    290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
            340                 345                 350

Asp Met Glu Gly Asn Pro Thr Tyr Gly Leu Ser Asn Thr Ala Thr Ala
        355                 360                 365

Val Ile Thr Val Thr Asp Val Asn Asp Asn Pro Pro Glu Phe Thr Ala
    370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                405                 410                 415

Asn Ala Val Tyr Arg Ile Ser Gly Gly Asp Pro Thr Gly Arg Phe Ala
            420                 425                 430

Ile Gln Thr Asp Pro Asn Ser Asn Asp Gly Leu Val Thr Val Val Lys
        435                 440                 445

Pro Ile Asp Phe Glu Thr Asn Arg Met Phe Val Leu Thr Val Ala Ala
    450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495

Phe Ala Pro Asn Pro Lys Ile Ile Arg Gln Glu Glu Gly Leu His Ala
            500                 505                 510
```

```
Gly Thr Met Leu Thr Thr Phe Thr Ala Gln Asp Pro Asp Arg Tyr Met
            515                 520                 525
Gln Gln Asn Ile Arg Tyr Thr Lys Leu Ser Asp Pro Ala Asn Trp Leu
        530                 535                 540
Lys Ile Asp Pro Val Asn Gly Gln Ile Thr Thr Ile Ala Val Leu Asp
545                 550                 555                 560
Arg Glu Ser Pro Asn Val Lys Asn Asn Ile Tyr Asn Ala Thr Phe Leu
                565                 570                 575
Ala Ser Asp Asn Gly Ile Pro Pro Met Ser Gly Thr Gly Thr Leu Gln
            580                 585                 590
Ile Tyr Leu Leu Asp Ile Asn Asp Asn Ala Pro Gln Val Leu Pro Gln
        595                 600                 605
Glu Ala Glu Thr Cys Glu Thr Pro Asp Pro Asn Ser Ile Asn Ile Thr
610                 615                 620
Ala Leu Asp Tyr Asp Ile Asp Pro Asn Ala Gly Pro Phe Ala Phe Asp
625                 630                 635                 640
Leu Pro Leu Ser Pro Val Thr Ile Lys Arg Asn Trp Thr Ile Thr Arg
                645                 650                 655
Leu Asn Gly Asp Phe Ala Gln Leu Asn Leu Lys Ile Lys Phe Leu Glu
            660                 665                 670
Ala Gly Ile Tyr Glu Val Pro Ile Ile Ile Thr Asp Ser Gly Asn Pro
        675                 680                 685
Pro Lys Ser Asn Ile Ser Ile Leu Arg Val Lys Val Cys Gln Cys Asp
690                 695                 700
Ser Asn Gly Asp Cys Thr Asp Val Asp Arg Ile Val Gly Ala Gly Leu
705                 710                 715                 720
Gly Thr Gly Ala Ile Ile Ala Ile Leu Leu Cys Ile Ile Ile Leu Leu
                725                 730                 735
Ile Leu Val Leu Met Phe Val Val Trp Met Lys Arg Arg Asp Lys Glu
            740                 745                 750
Arg Gln Ala Lys Gln Leu Leu Ile Asp Pro Glu Asp Asp Val Arg Asp
        755                 760                 765
Asn Ile Leu Lys Tyr Asp Glu Glu Gly Gly Gly Glu Asp Gln Asp
770                 775                 780
Tyr Asp Leu Ser Gln Leu Gln Gln Pro Asp Thr Val Glu Pro Asp Ala
785                 790                 795                 800
Ile Lys Pro Val Gly Ile Arg Arg Met Asp Glu Arg Pro Ile His Ala
                805                 810                 815
Glu Pro Gln Tyr Pro Val Arg Ser Ala Ala Pro His Pro Gly Asp Ile
            820                 825                 830
Gly Asp Phe Ile Asn Glu Gly Leu Lys Ala Ala Asp Asn Asp Pro Thr
        835                 840                 845
Ala Pro Pro Tyr Asp Ser Leu Leu Val Phe Asp Tyr Glu Gly Ser Gly
850                 855                 860
Ser Thr Ala Gly Ser Leu Ser Ser Leu Asn Ser Ser Ser Ser Gly Gly
865                 870                 875                 880
Glu Gln Asp Tyr Asp Tyr Leu Asn Asp Trp Gly Pro Arg Phe Lys Lys
                885                 890                 895
Leu Ala Asp Met Tyr Gly Gly Gly Asp Asp
            900                 905
```

<210> SEQ ID NO 4
<211> LENGTH: 4122
<212> TYPE: DNA
<213> ORGANISM: Homo sapiens
<220> FEATURE:
<223> OTHER INFORMATION: human N-cadherin variant, cadherin 2, type 1
      (CDH2), neuronal N-cadherin cDNA
<220> FEATURE:
<221> NAME/KEY: CDS
<222> LOCATION: (206)..(2926)
<223> OTHER INFORMATION: N-cadherin variant

<400> SEQUENCE: 4

```
tttgtcatca gctcgctctc cattggcggg gagcggagag cagcgaagaa ggggggtgggg    60 aggggagggg aagggaaggg ggtggaaact gcctggagcc gtttctccgc gccgctgttg   120
gtgctgccgc tgcctcctcc tcctccgccg ccgccgccgc cgccgccgcc tcctccggct   180
cttcgctcgg ccccctctccg cctccatgtg ccggatagcg ggagcgctgc ggaccctgct   240
gccgctgctg gcggccctgc ttcaggcgtc tgtagaggct tctggtgaaa tcgcattatg   300
caagactgga tttcctgaag atgtttacag tgcagtctta tcgaaggatg tgcatgaagg   360
acagcctctt ctcaatgtga agtttagcaa ctgcaatgga aaaagaaaag tacaatatga   420
gagcagtgag cctgcagatt ttaaggtgga tgaagatggc atggtgtatg ccgtgagaag   480 cttttccactc tcttctgagc atgccaagtt cctgatatat gcccaagaca agagaccca   540 ggaaaagtgg caagtggcag taaaattgag cctgaagcca accttaactg aggagtcagt   600
gaaggagtca gcagaagttg aagaaatagt gttcccaaga caattcagta agcacagtgg   660
ccacctacaa aggcagaaga gagactgggt catccctcca atcaacttgc agaaaactc   720 caggggacct tttcctcaag agcttgtcag gatcaggtct gatagagata aaaacctttc   780
actgcggtac agtgtaactg gccaggggc tgaccagcct ccaactggta tcttcattat   840 caacccccatc tcgggtcagc tgtcggtgac aaagcccctg gatcgcgagc agatagcccg   900
gtttcatttg agggcacatg cagtagatat taatggaaat caagtggaga ccccccattga   960 cattgtcatc aatgttattg acatgaatga caacagacct gagttcttac accaggtttg  1020
gaatgggaca gttcctgagg atcaaagcc tggaacatat gtgatgaccg taacagcaat  1080
tgatgctgac gatcccaatg ccctcaatgg gatgttgagg tacagaatcg tgtctcaggc  1140
tccaagcacc ccttcaccca acatgtttac aatcaacaat gagactggtg acatcatcac  1200
agtggcagct ggacttgatc gagaaaaagt gcaacagtat acgttaataa ttcaagctac  1260
agacatggaa ggcaatccca catatggcct ttcaaacaca gccacggccg tcatcacagt  1320
gacagatgtc aatgacaatc tccagagttt tactgccatg acgtttttatg gtgaagttcc  1380 tgagaacagg gtagacatca tagtagctaa tctaactgtg accgataagg atcaaccccca  1440 tacaccagcc tggaacgcag tgtacagaat cagtggcgga gatcctactg gacggttcgc  1500
catccagacc gaccccaaaca gcaacgacgg gttagtcacc gtggtcaaac caatcgactt  1560
tgaaacaaat aggatgtttg tccttactgt tgctgcagaa atcaagtgc cattagccaa  1620 gggaattcag caccgcctc agtcaactgc aaccgtgtct gttacagtta ttgacgtaaa  1680
tgaaaaccct tattttgccc ccaatccta a gatcattcgc caagaagaag gcttcatgc  1740 cggtaccatg ttgacaacat tcactgctca ggacccagat cgatatatgc agcaaaatat  1800
tagatacact aaaattatctg atcctgccaa ttggctaaaa atagatcctg tgaatggaca  1860
```

```
aataactaca attgctgttt tggaccgaga atcaccaaat gtgaaaaaca atatatataa    1920
tgctactttc cttgcttctg acaatggaat tcctcctatg agtggaacag gaacgctgca    1980
gatctattta cttgatatta atgacaatgc ccctcaagtg ttacctcaag aggcagagac    2040
ttgcgaaact ccagacccca attcaattaa tattacagca cttgattatg acattgatcc    2100
aaatgctgga ccatttgctt tgatcttcc tttatctcca gtgactatta agagaaattg     2160
gaccatcact cggcttaatg gtgattttgc tcagcttaat ttaaagataa aatttcttga    2220
agctggtatc tatgaagttc ccatcataat cacagattcg ggtaatcctc ccaaatcaaa    2280
tatttccatc ctgcgcgtga aggtttgcca gtgtgactcc aacggggact gcacagatgt    2340
ggacaggatt gtgggtgcgg ggcttggcac cggtgccatc attgccatcc tgctctgcat    2400
catcatcctg cttatccttg tgctgatgtt tgtggtatgg atgaaacgcc gggataaaga    2460
acgccaggcc aaacaacttt taattgatcc agaagatgat gtaagagata atattttaaa    2520
atatgatgaa gaaggtggag gagaagaaga ccaggactat gacttgagcc agctgcagca    2580
gcctgacact gtggagcctg atgccatcaa gcctgtggga atccgacgaa tggatgaaag    2640
acccatccac gctgagcccc agtatccggt ccgatctgca gccccacacc ctggagacat    2700
tggggacttc attaatgagg gccttaaagc ggctgacaat gaccccacag ctccaccata    2760
tgactccctg ttagtgtttg actatgaagg cagtggctcc actgctgggt ccttgagctc    2820
ccttaattcc tcaagtagtg gtggtgagca ggactatgat tacctgaacg actgggggcc    2880
acggttcaag aaacttgctg acatgtatgg tggaggtgat gactgaactt cagggtgaac    2940
ttggtttttg gacaagtaca aacaatttca actgatattc ccaaaaagca ttcagaagct    3000
aggctttaac tttgtagtct actagcacag tgcttgctgg aggctttggc ataggctgca    3060
aaccaatttg ggctcagagg gaatatcagt gatccatact gtttggaaaa acactgagct    3120
cagttacact tgaattttac agtacagaag cactgggatt ttatgtgcct ttttgtacct    3180
ttttcagatt ggaattagtt ttctgtttaa ggctttaatg gtactgattt ctgaaacgat    3240
aagtaaaaga caaatatttt tgtggtggga gcagtaagtt aaaccatgat atgcttcaac    3300
acgcttttgt tacattgcat ttgctttat taaaatacaa aattaaacaa acaaaaaaac     3360
tcatggagcg atttattat cttgggggat gagaccatga gattggaaaa tgtacattac      3420
ttctagtttt agactttagt ttgttttttt tttttcacta aaatcttaaa acttactcag    3480
ctggttgcaa ataaagggag ttttcatatc accaatttgt agcaaaattg aattttttca    3540
taaactagaa tgttagacac attttggtct taatccatgt acactttttt atttctgtat    3600
ttttccactt cactgtaaaa atagtatgtg tacataatgt tttattggca tagtctatgg    3660
agaagtgcag aaacttcaga acatgtgtat gtattatttg gactatggat tcaggttttt    3720
tgcatgttta tatctttcgt tatggataaa gtatttacaa aacagtgaca tttgattcaa    3780
ttgttgagct gtagttagaa tactcaattt ttaatttttt taatttttttt atttttatt    3840 ttcttttttgg tttggggagg gagaaaagtt cttagcacaa atgttttaca taatttgtac    3900
caaaaaaaaa aaaaggaaa ggaagaaag gggtggcctg acactggtgg cactactaag      3960
tgtgtgtttt ttaaaaaaaa aaatggaaaa aaaaaagctt ttaaactgga gagacttctg    4020
acaacagctt tgcctctgta ttgtgtacca gaatataaat gatacacctc tgaccccagc    4080
gttctgaata aaatgctaat tttggaaaaa aaaaaaaaaa aa                       4122
```